United States Patent
Iacoviello et al.

(10) Patent No.: US 11,862,338 B2
(45) Date of Patent: Jan. 2, 2024

(54) SYSTEMS AND METHODS FOR PROCESSING CONNECTIVITY VALUES BETWEEN SUB-PROCESSING REGIONS

(71) Applicant: ICAHN School of Medicine at Mount Sinai, New York, NY (US)

(72) Inventors: Brian M. Iacoviello, New York, NY (US); Dennis Charney, New York, NY (US)

(73) Assignee: Click Therapeutics, Inc., New York, NY (US)

(*) Notice: Subject to any disclaimer, the term of this patent is extended or adjusted under 35 U.S.C. 154(b) by 412 days.

(21) Appl. No.: 17/041,770

(22) PCT Filed: Mar. 27, 2019

(86) PCT No.: PCT/US2019/024407
§ 371 (c)(1),
(2) Date: Sep. 25, 2020

(87) PCT Pub. No.: WO2019/191311
PCT Pub. Date: Oct. 3, 2019

(65) Prior Publication Data
US 2021/0050109 A1     Feb. 18, 2021

Related U.S. Application Data

(60) Provisional application No. 62/649,469, filed on Mar. 28, 2018.

(51) Int. Cl.
*G16H 50/20* (2018.01)
*A61B 5/16* (2006.01)
(Continued)

(52) U.S. Cl.
CPC ............ *G16H 50/20* (2018.01); *A61B 5/165* (2013.01); *G16H 20/70* (2018.01); *G16H 50/50* (2018.01)

(58) Field of Classification Search
CPC .......................................... G16H 10/00–80/00
See application file for complete search history.

(56) References Cited

U.S. PATENT DOCUMENTS 9,211,212 B2    12/2015  Nofzinger et al.
9,292,858 B2     3/2016  Marci et al.
(Continued)

FOREIGN PATENT DOCUMENTS

JP     2014-522283 A    9/2014
JP     2015-170169 A    9/2015
WO    WO-2016089737 A1 * 6/2016  ........... A61B 5/0042

OTHER PUBLICATIONS

Tadayonnejad et al., "Brain Network Dysfunction in Late-Life Depression: A Literature Review," Journal of Geriatric Psychiatry and Neurology 2014, vol. 27(1) 5-12, DOI: 10.1177/0891988713516539 jgpn.sagepub.com (Year: 2014).*

(Continued)

*Primary Examiner* — Jonathon A. Szumny
(74) *Attorney, Agent, or Firm* — Foley & Lardner LLP

(57) ABSTRACT

The present disclosure relates to systems and methods for accessing a data structure including a subject identifier identifying a subject and a subject connectivity value derived from at least one of a scan or test provided to the subject, the subject connectivity value representing a magnitude of a connection associated with at least one sub-processing region of a nervous system of the subject; comparing the subject connectivity value to a connectivity threshold value to determine a classification of the subject; determining that the subject connectivity value exceeds the connectivity threshold value, storing in the data structure, an association between the subject identifier and a first classification value corresponding to a first classification or determining that the subject connectivity value is less than the connectivity threshold value, and storing in the data struc- (Continued)

ture, an association between the subject identifier and a second classification value corresponding to a second classification.

20 Claims, 12 Drawing Sheets

(51) Int. Cl.
  *G16H 20/70* (2018.01)
  *G16H 50/50* (2018.01)

(56) References Cited

U.S. PATENT DOCUMENTS

| | | | |
|---|---|---|---|
| 9,463,327 B2* | 10/2016 | Lempka | G16H 30/40 |
| 9,532,748 B2 | 1/2017 | Denison et al. | |
| 10,137,307 B2* | 11/2018 | Pascual-Leone | A61N 2/02 |
| 11,219,400 B2* | 1/2022 | Nenadovic | A61B 5/245 |
| 2006/0217781 A1* | 9/2006 | John | A61N 1/36017 |
| | | | 607/45 |
| 2011/0301431 A1 | 12/2011 | Greicius et al. | |
| 2013/0317580 A1* | 11/2013 | Simon | A61N 2/006 |
| | | | 607/115 |
| 2014/0107521 A1* | 4/2014 | Galan | A61B 5/4088 |
| | | | 600/544 |
| 2014/0364721 A1 | 12/2014 | Lee et al. | |
| 2017/0343634 A1* | 11/2017 | Lencz | A61B 5/0042 |
| 2019/0143119 A1* | 5/2019 | Dzirasa | A61N 1/36135 |
| | | | 607/2 |

OTHER PUBLICATIONS

Kito et al., "Cerebral blood flow ratio of the dorsolateral prefrontal cortex to the ventromedial prefrontal cortex as a potential predictor of treatment response to transcranial magnetic stimulation in depression," Brain Stimulation (2012) 5, 547-53; doi:10.1016/j.brs.2011. 09.004. (Year: 2012).*
Liston et al., "Default Mode Network Mechanisms of Transcranial Magnetic Stimulation in Depression," Biol Psychiatry 2014; 76:517-526; http://dx.doi.org/10.1016/j.biopsych.2014.01.023. (Year: 2014).*
Cao et al., "Effects of Cognitive Training on Resting-State Functional Connectivity of Default Mode, Salience, and Central Executive," Frontiers in Aging Neuroscience | www.frontiersin.org Apr. 1, 2016 | vol. 8 | Article 70; doi: 10.3389/fnagi.2016.00070. (Year: 2016).*
Kucyi et al., "Enhanced Medial Prefrontal-Default Mode Network Functional Connectivity in Chronic Pain and Its Association with Pain Rumination," The Journal of Neuroscience, Mar. 12, 2014 • 34(11):3969-3975 • 3969; DOI:10.1523/JNEUROSCI.5055-13. 2014. (Year: 2014).*
Leech et al., "Fractionating the Default Mode Network: Distinct Contributions of the Ventral and Dorsal Posterior Cingulate Cortex to Cognitive Control," The Journal of Neuroscience, Mar. 2, 2011 • 31(9):3217-3224 • 3217; DOI:10.1523/JNEUROSCI.5626-10.2011. (Year: 2011).*
Grimm et al., "Imbalance between Left and Right Dorsolateral Prefrontal Cortex in Major Depression is Linked to Negative Emotional Judgment: An fMRI Study in Severe Major Depressive Disorder," Biol Psychiatry 2008;63:369-376 doi:10.1016/j.biopsych. 2007.05.033. (Year: 2008).*
Fox et al., "Measuring and manipulating brain connectivity with resting state functional connectivity magnetic resonance imaging (fcMRI) and transcranial magnetic stimulation (TMS)," NeuroImage 62 (2012) 2232-2243; doi:10.1016/j.neuroimage.2012.03.035. (Year: 2012).*
Lemogne et al., "Medial prefrontal cortex and the self in major depression," Journal of Affective Disorders 136 (2012) e1-e11; doi:10.1016/j.jad.2010.11.034. (Year: 2012).*
Holmes et al., "Response conflict and frontocingulate dysfunction in unmedicated participants with major depression," Neuropsychologia 46 (2008) 2904-2913; doi:10.1016/j.neuropsychologia.2008.05. 028. (Year: 2008).*
Mulders et al., "Resting-state functional connectivity in major depressive disorder: A review," Neuroscience and Biobehavioral Reviews 56 (2015) 330-344; http://dx.doi.org/10.1016/j.neubiorev. 2015.07.014. (Year: 2015).*
Lui et al., "Resting-State Functional Connectivity in Treatment-Resistant Depression," Am J Psychiatry 2011; 168:642-648; (Year: 2011).*
Sikora et al., "Salience Network Functional Connectivity Predicts Placebo Effects in Major Depression," Biological Psychiatry: Cognitive Neuroscience and Neuroimaging Jan. 2016;1:68-76; http:// dx.doi.org/10.1016/j.bpsc.2015.10.002. (Year: 2016).*
V. Menon, "Salience Network," Brain Mapping: An Encyclopedic Reference, (2015), vol. 2, pp. 597-611; http://dx.doi.org/10.1016/ B978-0-12-397025-1.00052-X. (Year: 2015).*
Fischer et al., "The Clinical Applicability of Functional Connectivity in Depression: Pathways Toward More Targeted Intervention," Biological Psychiatry: Cognitive Neuroscience and Neuroimaging May 2016;1:262-270; http://dx.doi.org/10.1016/j.bpsc.2016.02. 004. (Year: 2016).*
Koenigs et al., "The functional neuroanatomy of depression: Distinct roles for ventromedial and dorsolateral prefrontal cortex," Behav Brain Res. Aug. 12, 2009; 201(2): 239-243. doi:10.1016/j. bbr.2009.03.004. (Year: 2009).*
Robinson et al., "Towards a mechanistic understanding of pathological anxiety: the dorsal medial prefrontal-amygdala 'aversive amplification' circuit in unmedicated generalized and social anxiety disorders," Lancet Psychiatry. Sep. 1, 2014; 1(4): 294-302. doi:10. 1016/S2215-0366(14)70305-0. (Year: 2014).*
Wagner et al., "Treatment Associated Changes of Functional Connectivity of Midbrain/Brainstem Nuclei in Major Depressive Disorder," Scientific Reports | 7: 8675 | DOI:10.1038/s41598-017-09077-5. (Year: 2017).*
International Preliminary Report regarding PCT/US2019/024407 dated Sep. 29, 2020.
International Search Report on PCT/US2019/024407 dated Mar. 10, 2019.
Mason et al: "Brain Connectivity changes occurring following cognitive behavioural therapy for psychosis predict long-term recovery", Translation Psychiatry, vol. 7,No. 1, Jan. 17, 2017, abstract,p. 1.
Office Action on TW Application No. 108111081 dated May 14, 2020.
Richiardi et al, "Low-Dimensional embedding of functional connectivity graphs for brain state decoding," 2010, First Workshop On, NJ on Aug. 22, 2010.
Sarah Opialla et al., "Neural circuits of emotion regulation: a comparison of mindfulness-based and cognitive reappraisal strategies," European Archives of Psychiatry and Clinical Neuroscience vol. 265, pp. 45-55, 2015.
Written Opinion of the International Searching Authority on PCT/ US2019/024407 dated Mar. 10, 2019.
Examination Report on IN 202037046378 dated Sep. 15, 2022.
Foreign Action other than Search Report on JP Appl. No. 2020-552302 dated Feb. 14, 2023.

* cited by examiner

| Region | Laterality | Co-ordinates | | | Cluster Size | Cluster level p-value | Peak T-value |
|---|---|---|---|---|---|---|---|
| | | x | y | z | | | |
| Baseline > Post-treatment | | | | | | | |
| Dorsolateral prefrontal Cortex | Right | 46 | 12 | 52 | 149 | 0.009 | 5.31 |
| | Right | 16 | 32 | 52 | 149 | 0.009 | 4.68 |
| Inferior Parietal Lobe | Left | -54 | -62 | 30 | 91 | 0.021 | 5.04 |
| | Right | 52 | -56 | 46 | 103 | 0.018 | 3.95 |
| Middle Temporal Gyrus | Left | -48 | -28 | -12 | 66 | 0.034 | 4.92 |
| Post-treatment > Baseline | | | | | | | |
| Dorsal anterior Cingulate Cortex | Bilateral | 0 | -6 | 42 | 73 | 0.032 | 4.91 |

*Note:* Coordinates are shown in MNI space; x=axial; y=coronal; z=sagittal; Cluster-level inference was used to identify spatially contiguous voxels at a threshold of $p < 0.001$, without correction, and then a familywise error-corrected cluster-extent threshold of $p < 0.05$ was applied to infer statistical significance.

FIG. 4

| | |
|---|---|
| n | 14 |
| Gender | 12 Female, 2 Male |
| Age | 36.64 years (8.37) |
| Race | Caucasian: 7<br>More than one race: 3<br>African American: 2<br>Asian: 1<br>Unreported: 1 |
| Ethnicity | Non-Hispanic: 10<br>Hispanic: 3<br>Not Reported: 1 |
| Baseline Depression Severity (Ham-D) | 19.14 (2.60) |
| Outcome Depression Severity (Ham-D) | 11.43 (5.12) |
| Duration of current MDD episode (months) | 21.07 months (24.10) |
| Number of lifetime MDD episodes | 2.77 (1.69) |
| Age at first MDD episode | 25.36 (13.12) |
| *Note:* Values represent mean (SD) or n's. ||

FIG. 5

BEFORE TREATMENT

No Medial Temporal Network

AFTER TREATMENT

Partial Medial Temporal Network

| Subject Identifier | First Connectivity Value | Rank | Classification | Second Connectivity Value | Efficacy |
|---|---|---|---|---|---|
| Subject 1 | 10 | 3 | Eligible | 20 | Y |
| Subject 2 | 6 | 2 | Ineligible | 8 | N |
| Subject 3 | 15 | 4 | Eligible | 17 | N |
| ... | ... | ... | ... | ... | ... |
| Subject n | 2 | 1 | Ineligible | 10 | Y |

FIG. 9

SYSTEMS AND METHODS FOR PROCESSING CONNECTIVITY VALUES BETWEEN SUB-PROCESSING REGIONS

CROSS-REFERENCE TO RELATED APPLICATIONS

This application is a national stage application under 35 U.S.C. § 371 of International Application No. PCT/US2019/024407, filed Mar. 27, 2019, which claims the benefit of and priority to U.S. Provisional Application No. 62/649,469, filed Mar. 28, 2018, each of which is incorporated by reference herein in its entirety.

GOVERNMENT SUPPORT

This invention was made with government support under grant number 5K23MH099223, awarded by the National Institutes of Health. The government has certain rights in the invention.

BACKGROUND

The following description of the background of the present technology is provided simply as an aid in understanding the present technology and is not admitted to describe or constitute prior art to the present technology.

Connectivity values can be determined using one or more methods, such as imaging. The connectivity values can indicate a condition. Certain conditions can be improved by affecting changes in the connectivity values.

SUMMARY OF THE PRESENT TECHNOLOGY

In one aspect, the present disclosure provides a data processing system with a hardware storage device storing one or more data structures and executable logic for processing data values stored in the one or more data structure. The data processing system includes a hardware storage device storing one or more data structures, each data structure storing keyed data, with an item of keyed data including a key that represents a subject, and with the hardware storage device further storing executable logic including classification rules. The data processing system further includes one or more data processors for accessing, from the hardware storage device, at least one of the one or more data structures, and for retrieving, from the at least one of the one or more data structures accessed, keyed data for a particular subject, with the retrieved keyed data including a subject connectivity value derived from at least one of a scan or test provided to a subject represented by a key included in the retrieved keyed data, the subject connectivity value representing a magnitude of a connection associated with at least one sub-processing region of a nervous system of the subject. The data processing system further includes an executable logic engine configured to execute the executable logic against the keyed data to apply the classification rules to the subject connectivity value and to a connectivity threshold value to determine a classification of the subject. The hardware storage device storing is further configured to store, in a data structure, an association between a key represented in the keyed data and a first classification value corresponding to a first classification, when subject connectivity value exceeds the connectivity threshold value. The hardware storage device storing is further configured to store, in a data structure, an association between a key represented in the keyed data and a second classification value corresponding to a second classification, when subject connectivity value is less than the connectivity threshold value.

In some embodiments, the at least one sub-processing region includes the dorsolateral prefrontal cortex (DPFC) and the amygdala (AMG), the subject connectivity value and the connectivity threshold value represent an effective connectivity between the DPFC and the AMG and an effective connectivity threshold value between the DPFC and the AMG, and the first classification value indicates that the subject is ineligible, and the second classification value indicates that the subject is eligible.

In some embodiments, the at least one sub-processing region includes the anterior cingulate cortex (dACC) and the amygdala (AMG), the subject connectivity value and the connectivity threshold value, respectively, represent an effective connectivity between the dACC and the AMG and an effective connectivity threshold value between the dACC and the AMG, and the first classification value indicates that the subject is eligible, and the second classification value indicates that the subject is ineligible.

In some embodiments, the at least one sub-processing region includes the default mode resting state network (DMN), the subject connectivity value and the connectivity threshold value, respectively, represent a functional connectivity within the DMN and a functional connectivity threshold value associated with the DMN, and the first classification value indicates that the subject is eligible, and the second classification value indicates that the subject is ineligible.

In some embodiments, the at least one sub-processing region includes the salience resting state network (SAL), the subject connectivity value and the connectivity threshold value, respectively, represent a functional connectivity within the SAL and a functional connectivity threshold value associated with the SAL, and the first classification value indicates that the subject is eligible, and the second classification value indicates that the subject is ineligible.

In some embodiments, the at least one sub-processing region includes the left central executive network (LCEN) and the right central executive network (RCEN), the subject connectivity value and the connectivity threshold value, respectively, represent an integration between the LCEN and the RCEN and an integration threshold value between the LCEN and the RCEN, and the first classification value indicates that the subject is ineligible, and the second classification value indicates that the subject is eligible.

In some embodiments, the at least one sub-processing region includes the dorsal default mode resting state network (dDMN) and the ventral default mode resting state network (vDMN), the subject connectivity value and the connectivity threshold value, respectively, represent an integration between the dDMN and the vDMN and an integration threshold value between the dDMN and the vDMN, and the first classification value indicates that the subject is ineligible, and the second classification value indicates that the subject is eligible.

In some embodiments, the at least one sub-processing region includes the left central executive network (LCEN) and the ventral default mode resting state network (vDMN), the subject connectivity value and the connectivity threshold value, respectively, represent an integration between the LCEN and the vDMN and an integration threshold value between the LCEN and the vDMN, and the first classification value indicates that the subject is ineligible, and the second classification value indicates that the subject is eligible.

In some embodiments, the at least one sub-processing region includes the left central executive network (LCEN) and the salience resting state network (SAL), the subject connectivity value and the connectivity threshold value, respectively, represent an integration between the LCEN and the SAL and an integration threshold value between the LCEN and the SAL, and the first classification value indicates that the subject is ineligible, and the second classification value indicates that the subject is eligible.

In another aspect, the present disclosure provides a method for classifying a subject based on connectivity values. The method includes accessing, by a data processing system including one or more processors, a data structure including a subject identifier identifying a subject and a subject connectivity value derived from at least one of a scan or test provided to the subject, the subject connectivity value representing a magnitude of a connection associated with at least one sub-processing region of a nervous system of the subject. The method further includes comparing, by the data processing system, the subject connectivity value to a connectivity threshold value to determine a classification of the subject. The method also includes responsive to determining, by the data processing system, that the subject connectivity value exceeds the connectivity threshold value, storing, by the data processing system, in the data structure, an association between the subject identifier and a first classification value corresponding to a first classification. The method also includes responsive to determining, by the data processing system, that the subject connectivity value is less than the connectivity threshold value, storing, by the data processing system, in the data structure, an association between the subject identifier and a second classification value corresponding to a second classification.

In some embodiments, the at least one sub-processing region includes the dorsolateral prefrontal cortex (DPFC) and the amygdala (AMG), the subject connectivity value and the connectivity threshold value represent an effective connectivity between the DPFC and the AMG and an effective connectivity threshold value between the DPFC and the AMG, and the first classification value indicates that the subject is ineligible, and the second classification value indicates that the subject is eligible.

In some embodiments, the at least one sub-processing region includes the anterior cingulate cortex (dACC) and the amygdala (AMG), the subject connectivity value and the connectivity threshold value, respectively, represent an effective connectivity between the dACC and the AMG and an effective connectivity threshold value between the dACC and the AMG, and the first classification value indicates that the subject is eligible, and the second classification value indicates that the subject is ineligible.

In some embodiments, the at least one sub-processing region includes the default mode resting state network (DMN), the subject connectivity value and the connectivity threshold value, respectively, represent a functional connectivity within the DMN and a functional connectivity threshold value associated with the DMN, and the first classification value indicates that the subject is eligible, and the second classification value indicates that the subject is ineligible.

In some embodiments, the at least one sub-processing region includes the salience resting state network (SAL), the subject connectivity value and the connectivity threshold value, respectively, represent a functional connectivity within the SAL and a functional connectivity threshold value associated with the SAL, and the first classification value indicates that the subject is eligible, and the second classification value indicates that the subject is ineligible.

In some embodiments, the at least one sub-processing region includes the left central executive network (LCEN) and the right central executive network (RCEN), the subject connectivity value and the connectivity threshold value, respectively, represent an integration between the LCEN and the RCEN and an integration threshold value between the LCEN and the RCEN, and the first classification value indicates that the subject is ineligible, and the second classification value indicates that the subject is eligible.

In some embodiments, the at least one sub-processing region includes the dorsal default mode resting state network (dDMN) and the ventral default mode resting state network (vDMN), the subject connectivity value and the connectivity threshold value, respectively, represent an integration between the dDMN and the vDMN and an integration threshold value between the dDMN and the vDMN, and the first classification value indicates that the subject is ineligible, and the second classification value indicates that the subject is eligible.

In some embodiments, the at least one sub-processing region includes the left central executive network (LCEN) and the ventral default mode resting state network (vDMN), the subject connectivity value and the connectivity threshold value, respectively, represent an integration between the LCEN and the vDMN and an integration threshold value between the LCEN and the vDMN, and the first classification value indicates that the subject is ineligible, and the second classification value indicates that the subject is eligible.

In some embodiments, the at least one sub-processing region includes the left central executive network (LCEN) and the salience resting state network (SAL), the subject connectivity value and the connectivity threshold value, respectively, represent an integration between the LCEN and the SAL and an integration threshold value between the LCEN and the SAL, and the first classification value indicates that the subject is ineligible, and the second classification value indicates that the subject is eligible.

In some embodiments, the subject connectivity value is a first subject connectivity value and the connectivity threshold value is a first connectivity threshold value, the method further includes accessing, by the data processing system, the data structure including a second subject connectivity value derived from at least one scan or test provided to the subject, the second subject connectivity value representing a magnitude of a connection associated with another at least one sub-processing region of the nervous system of the subject. The method also includes comparing, by the data processing system, the second subject connectivity value. The method further includes responsive to determining, by the data processing system, that the first subject connectivity value exceeds the first connectivity threshold value and the second subject connectivity value is less than the second connectivity threshold value, storing, by the data processing system, in the data structure, the association between the subject identifier and the first classification value corresponding to the first classification. The method also includes responsive to determining, by the data processing system, that the first subject connectivity value is less than the first connectivity threshold value and the second subject connectivity value exceeds the second connectivity threshold value, storing, by the data processing system, in the data structure, the association between the subject identifier and the second classification value corresponding to the second classification.

In some embodiments, the at least one sub-processing region includes the dorsolateral prefrontal cortex (DPFC) and the amygdala (AMG), the first subject connectivity value and the first connectivity threshold value represent an effective connectivity between the DPFC and the AMG and an effective connectivity threshold value between the DPFC and the AMG, the another at least one sub-processing region includes the anterior cingulate cortex (dACC) and the amygdala (AMG), the second subject connectivity value and the second connectivity threshold value, respectively, represent an effective connectivity between the dACC and the AMG and an effective connectivity threshold value between the dACC and the AMG, and the first classification value indicates that the subject is ineligible, and the second classification value indicates that the subject is eligible.

In yet another aspect, the present disclosure provides a method for ranking candidates based on connectivity values. The method includes identifying, by a data processing system including one or more processors, from a data structure, a plurality of subject connectivity values associated with a plurality of subject identifiers corresponding to a plurality of subjects, each subject connectivity value in the plurality of subject connectivity values representing a magnitude of a connection associated with at least one sub-processing region of a nervous system of a respective subject of the plurality of subjects. The method further includes assigning, by the data processing system, to each subject identifier in the data structure, a rank based on the subject connectivity value. The method also includes selecting, by the data processing system, a subset of subjects, each subject of the subset selected based on a difference between the connectivity threshold value and the subject connectivity value. The method further includes generating, by the data processing system, an ordered list of subject identifiers corresponding to the selected subset of subjects, the subject identifiers arranged based on the rank assigned to the respective subject identifier.

In some embodiments, the at least one sub-processing region includes the dorsolateral prefrontal cortex (DPFC) and the amygdala (AMG), the plurality of subject connectivity values and the connectivity threshold value represent effective connectivity between the DPFC and the AMG for the respective plurality of subjects and an effective connectivity threshold value between the DPFC and the AMG, and subject connectivity values associated with the selected subset of subjects are below the connectivity threshold value.

In some embodiments, the at least one sub-processing region includes the anterior cingulate cortex (dACC) and the amygdala (AMG), the plurality of subject connectivity values and the connectivity threshold value represent effective connectivity between the dACC and the AMG for the respective plurality of subjects and an effective connectivity threshold value between the dACC and the AMG, and subject connectivity values associated with the selected subset of subjects are above the connectivity threshold value.

In some embodiments, the at least one sub-processing region includes the default mode resting state network (DMN), the plurality of subject connectivity values and the connectivity threshold value represent functional connectivity within the DMN for the respective plurality of subjects and a functional connectivity threshold value within the DMN, and subject connectivity values associated with the selected subset of subjects are above the connectivity threshold value.

In some embodiments, the at least one sub-processing region includes the salience resting state network (SAL), the plurality of subject connectivity values and the connectivity threshold value represent functional connectivity within the SAL for the respective plurality of subjects and a functional connectivity threshold value within the SAL, and subject connectivity values associated with the selected subset of subjects are above the connectivity threshold value.

In some embodiments, the at least one sub-processing region includes the left central executive network (LCEN) and the right central executive network (RCEN), the plurality of subject connectivity values and the connectivity threshold value represent integration between the LCEN and the RCEN for the respective plurality of subjects and an integration threshold value between the LCEN and the RCEN, and subject connectivity values associated with the selected subset of subjects are below the connectivity threshold value.

In some embodiments, the at least one sub-processing region includes the dorsal default mode resting state network (dDMN) and the ventral default mode resting state network (vDMN), the plurality of subject connectivity values and the connectivity threshold value represent integration between the dDMN and the vDMN for the respective plurality of subjects and an integration threshold value between the dDMN and the vDMN, and subject connectivity values associated with the selected subset of subjects are below the connectivity threshold value.

In some embodiments, the at least one sub-processing region includes the left central executive network (LCEN) and the ventral default mode resting state network (vDMN), the plurality of subject connectivity values and the connectivity threshold value represent integration between the LCEN and the vDMN for the respective plurality of subjects and an integration threshold value between the LCEN and the vDMN, and subject connectivity values associated with the selected subset of subjects are below the connectivity threshold value.

In some embodiments, the at least one sub-processing region includes the left central executive network (LCEN) and the salience resting state network (SAL), the plurality of subject connectivity values and the connectivity threshold value represent integration between the LCEN and the SAL for the respective plurality of subjects and an integration threshold value between the LCEN and the SAL, and subject connectivity values associated with the selected subset of subjects are below the connectivity threshold value.

In yet another aspect, the present disclosure provides a method for determining efficacy of a treatment based on connectivity values. The method includes identifying, by the data processing system including one or more processors, a first connectivity value of a subject, the first connectivity value representing a first magnitude of a connection associated with at least one sub-processing region of a nervous system of a subject at a first time. The method further includes identifying, by the data processing system, a second connectivity value of the subject, the second connectivity value representing a second magnitude of the connection associated with the at least one sub-processing region of the nervous system of the subject at a second time after the subject has been exposed to cognitive-emotional training. The method also includes determining, by the data processing system, a difference between the first connectivity value and the second connectivity. The method further includes responsive to determining that the difference exceeds a threshold value, storing, by the data processing system, in a data structure including a subject identifier identifying the subject, and an association between the subject identifier and a first classification value corresponding to a first classification. The method additionally includes responsive to determining that the difference is less than the threshold value, storing, in the data structure including the subject identifier, and an association between the subject identifier and a second classification value corresponding to a second classification.

In some embodiments, the at least one sub-processing region includes the dorsolateral prefrontal cortex (DPFC) and the amygdala (AMG), the first connectivity value and the second connectivity value represent an effective connectivity between the DPFC and the AMG of the subject at the first time and the second time, respectively.

In some embodiments, the at least one sub-processing region includes the anterior cingulate cortex (dACC) and the amygdala (AMG), the first connectivity value and the second connectivity value represent an effective connectivity between the DPFC and the AMG of the subject at the first time and the second time, respectively.

In some embodiments, the at least one sub-processing region includes the default mode resting state network (DMN), the first connectivity value and the second connectivity value, respectively, represent a functional connectivity within the DMN of the subject at the first time and the second time, respectively.

In some embodiments, the at least one sub-processing region includes the salience resting state network (SAL), the first connectivity value and the second connectivity value represent a functional connectivity within the SAL of the subject at the first time and the second time, respectively.

In some embodiments, the at least one sub-processing region includes the left central executive network (LCEN) and the right central executive network (RCEN), the first connectivity value and the second connectivity value represent an integration between the LCEN and the RCEN of the subject at the first time and the second time, respectively.

In some embodiments, the at least one sub-processing region includes the dorsal default mode resting state network (dDMN) and the ventral default mode resting state network (vDMN), the first connectivity value and the second connectivity value represent an integration between the dDMN and the vDMN of the subject at the first time and the second time, respectively.

In some embodiments, the at least one sub-processing region includes the left central executive network (LCEN) and the ventral default mode resting state network (vDMN), the first connectivity value and the second connectivity value represent an integration value between the LCEN and the vDMN of the subject at the first time and the second time, respectively.

In some embodiments, the at least one sub-processing region includes the left central executive network (LCEN) and the salience resting state network (SAL), the first connectivity value and the second connectivity value represent an integration value between the LCEN and the SAL of the subject at the first time and the second time, respectively.

In yet another aspect, the present disclosure provides a method for increasing effective connectivity between DPFC and AMG and decreasing effective connectivity between dACC and AMG in a subject suffering from an Affective Disorder for an effective amount of time.

In yet another aspect, the present disclosure provides a method for decreasing functional connectivity in at least one of the dDMN and the SAL in a subject suffering from an Affective Disorder for an effective amount of time.

In yet another aspect, the present disclosure provides a method for increasing integration across at least one pair of the LCEN and the RCEN, the dDMN and the vDMN, the LCEN and the vDMN, or the LCEN and the SAL in a subject suffering from an Affective Disorder for an effective amount of time.

In any of the above embodiments of the methods disclosed herein, the Affective Disorder may be major depressive disorder (MDD), bipolar disorder, post-traumatic stress disorder (PTSD), general anxiety disorder, social phobia, obsessive compulsive disorder, treatment resistant depression, or borderline personality disorder.

BRIEF DESCRIPTION OF THE DRAWINGS

FIG. 2A illustrates the spatial distribution of the resting-state networks examined herein. FIG. 2B demonstrates the effect size of post-treatment changes observed in within-network and between-network functional connectivity. Only networks which yielded an effect size>0.3 are shown. Abbreviations: dDMN: dorsal default mode network; vDMN: ventral default mode network; SAL: salience network; LCEN: left central executive network; RCEN: right central executive network.

FIG. 3A shows a schematic representation of the changes in pre-to-post effective connectivity between dACC, DPFC and AMG during the EFMT. A solid arrow exhibits enhanced connectivity, whereas a dashed arrow exhibits reduced connectivity. FIG. 3B demonstrates changes in effective connectivity during EFMT task completion from pre-to-post EFMT treatment. AMG: amygdala, dACC: dorsal anterior cingulate cortex, DPFC=dorsolateral prefrontal cortex.

FIG. 4 illustrates differences in task-related brain activation at baseline and post-treatment. Coordinates are shown in MNI space; x=axial; y=coronal; z=sagittal; Cluster-level inference was used to identify spatially contiguous voxels at a threshold of $p<0.001$, without correction, and then a familywise error-corrected cluster-extent threshold of $p<0.05$ was applied to infer statistical significance.

FIG. 5 shows the demographic and clinical characteristics of the MDD participants in the study.

FIG. 9 shows an example data structure.

DETAILED DESCRIPTION

Figure 1:
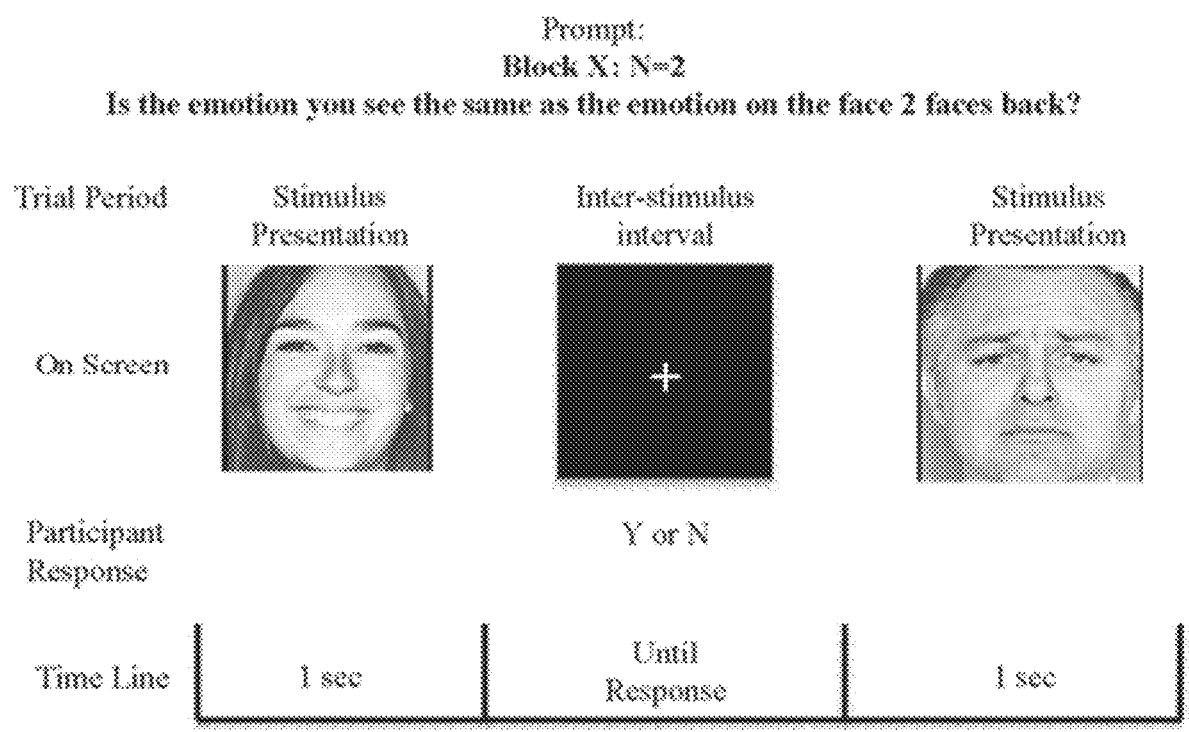
FIG. 1 illustrates a non-limiting, exemplary EFMT trial. Participants observed an expression of facial affect shown on screen for is and identified the emotion expressed. Participants then compared the observed emotion to the emotion observed N faces prior, for example N=2 faces prior.

It is to be appreciated that certain aspects, modes, embodiments, variations and features of the present methods are described below in various levels of detail in order to provide a substantial understanding of the present technology.

There is an urgent need for more efficacious treatments for psychiatric disorders characterized by negative affect (e.g., Affective Disorder), such as major depressive disorder (MDD), post-traumatic stress disorder, and anxiety disorders. Such ADs are common, disabling and costly. Indeed, an estimated 350 million people worldwide suffer from depression, which is the leading cause of disability in Americans ages 15-44.

Major depressive disorder (MDD) is among the leading causes of disability worldwide and is as associated with both significant functional impairment and reduced quality of life (WHO, 2001). MDD is a highly prevalent mental illness, affecting approximately 17% of the population across the lifespan, and frequently following a recurrent and chronic course (Kessler et al., *JAMA*. 289, 3095-3105 (2003)). Despite the availability of established treatments, it is estimated that only about one third of patients with MDD achieve remission (Trivedi et al., *Am J Psychiatry* 163, 28-40 (2006); Rush et al., *Am J Psychiatry* 163, 1905-1917 (2006)). Accordingly, methods and systems that assign the appropriate therapeutic intervention to a particular subject are warranted.

The present disclosure demonstrates that cognitive-emotional training is associated with changes in short-term plasticity of brain networks implicated in an Affective Disorder, such as MDD, bipolar disorder, post-traumatic stress disorder (PTSD), general anxiety disorder, social phobia, obsessive compulsive disorder, treatment resistant depression, or borderline personality disorder. Fourteen MDD patients received cognitive-emotional training (e.g., that Emotional Faces Memory Task (EFMT) training) as monotherapy over a 6-week period. Patients were scanned at baseline and post-treatment to identify changes in resting-state functional connectivity and effective connectivity during emotional working memory processing. Compared to baseline, patients showed post-treatment reduced connectivity within resting-state networks involved in self-referential and salience processing and greater integration across the functional connectome at rest. Moreover, a post-treatment increase in the EFMT-induced modulation of connectivity was observed between the cortical control and limbic brain regions, which was associated with clinical improvement. These results demonstrate that cognitive-emotional training enhances the functional integration of resting-state networks and the effective connectivity from cortical control brain regions to regions involved in emotional responses, and that these changes in connectivity parameters are related to symptomatic improvement. Cognitive-emotional training is also associated with changes in short-term plasticity of brain networks implicated in other disorders. For example, the disorders can include anxiety disorders, such as generalized anxiety disorder (GAD), social phobia, borderline personality disorder, and post-traumatic stress disorder (PTSD), etc.

The systems and methods disclosed herein are useful for rapidly and accurately detecting an Affective Disorder based on a patient's effective connectivity and/or functional connectivity between select sub-processing regions. Moreover, the systems and methods of the present technology permit clinicians to rapidly assign suitable therapeutic interventions (e.g., cognitive-emotional therapy) to patients with Affective Disorders. The systems and methods described herein also assist with mitigating delays in clinical decision-making with respect to maintaining or modifying a therapeutic regimen (e.g., altering, substituting, or discontinuing a particular course of therapy, or incorporating an additional therapy) of a patient suffering from an Affective Disorder, thereby ensuring patient safety, and reducing the overall risk of suicide.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the terms "brain activation" or "brain activity" refer to the electrical activity of one or more neurons in at least one brain region and the corresponding metabolic changes observed in a subject in response to an internal or external stimulus.

As used herein, "cognitive-emotional training" refers to the performance of cognitive or emotion-oriented tasks for the purpose of inducing activation in specific brain regions, and aiming to modulate the activation patterns within/between regions over time (harnessing brain plasticity) to induce symptom improvement in psychiatric conditions.

As used herein, a "control" is an alternative sample used in an experiment for comparison purpose. A control can be "positive" or "negative." For example, where the purpose of the experiment is to determine a correlation of the efficacy of a therapeutic intervention for a particular type of disease, a positive control (an intervention known to exhibit the desired therapeutic effect) and a negative control (a subject or a sample that does not receive the therapy or receives a placebo) are typically employed.

As used herein, "effective connectivity" or "EC" refers to the influence one neural system or brain region has, or exerts, on another neural system or brain region. EC depends on and tests an a priori defined model for the influence between brain regions/neural systems, rather than reporting an observed correlation (as in FC). In order to determine whether one brain region influences another, the correlation of neural activity between two brain regions is measured during a specific behavior or cognitive task that is known or believed to activate the network or system (e.g., working memory). In some embodiments, effective connectivity can be measured from fMRI data. Methods for measuring and interpreting EC are described in Friston, *Human Brain Mapping* 2:56-78(1994). Effective connectivity can be considered an index of short-term neural-network level plasticity (Stephan et al. *Biological Psychiatry* 59, 929-939 (2006); Friston, *Brain Connect.* 1(1):13-36 (2011)). This short-term plasticity represents a fundamental mechanism by which the brain alters or contextualizes its connectivity and function in response to external or internal cues (Salinas & Sejnowski, *Neuroscientist* 7, 430-440 (2001)).

As used herein, "functional connectivity" or "FC" refers to the temporal correlations between spatially remote neurophysiological events (activations of distinct brain regions). FC is a statement about observed correlations. Functional connectivity can be measured using functional magnetic resonance imaging (fMRI) where a blood oxygen level dependent (BOLD) signal is measured as a quantitative indicator of neural activity in a specific brain region of interest. Any signal of neural activity (electrophysiological signals such as EEG) can also be used to calculate FC. Correlation between signals in distinct brain regions is calculated to estimate FC. Methods for measuring and interpreting FC are described in Friston, *Human Brain Mapping* 2:56-78(1994).

As used herein, "integration" refers to the degree of functional connectivity or effective connectivity within a single network or brain region, or between multiple networks or brain regions.

As used herein, a "neuron" is an electrically excitable cell of the nervous system that communicates with other cells via synapses. A typical neuron comprises a cell body, several short branches processes (dendrites), and one long process (axon).

As used herein, the term "plasticity" refers to the strengthening or weakening of neuronal synapses over time.

As used herein, a "synapse" is a specialized region between an axon terminus of a neuron and an adjacent neuron or target effector cell (e.g., muscle cell) across which impulses (i.e., electrical signals and/or chemical signals) are transmitted. An impulse may be conducted by a neurotransmitter, or may be transmitted via gap junctions connecting the cytoplasms of pre- and post-synaptic cells.

As used herein, the terms "individual", "patient", or "subject" can be an individual organism, a vertebrate, a mammal, or a human. In some embodiments, the individual, patient or subject is a human.

As used herein, an "effective amount of time" refers to a duration based on a combination of one or more of a frequency, a length, and/or content (e.g., number or quality of images) of a cognitive-emotional training session, that can achieve a desired endpoint of effective connectivity, functional connectivity, or integration in at least one sub-processing region of the nervous system of a subject.

Altered Brain Activation in MDD

Numerous studies have shown that patients with MDD exhibit persistent deficits in cognitive control (the capacity to maintain and manipulate information) in the presence of emotionally salient stimuli, and that such deficits are associated with illness severity (Hamilton et al. *Am J Psychiatry.* 169(7):693-703 (2012); Bora et al. *Psychol Med.* 43(10): 2017-26 (2013)). Functional magnetic resonance imaging (fMRI) studies in MDD have shown that dorsal cortical regions known to subserve cognitive control are hypoactive, whereas regions involved in emotion processing, particularly the amygdala (AMG), are hyperactive (Deiner et al., *Neuroimage.* 61(3):677-85 (2012); Fitzgerald et al., *Hum. Brain Mapp.* 29, 683-695 (2008)). These abnormalities have been observed across multiple tasks but have been most commonly studied using working memory (Wang et al. *Prog Neuropsychopharmacol Biol Psychiatry.* 56:101-8 (2015)) and facial affect processing paradigms (Stuhrmann et al. *Biol Mood Anxiety Disord.* 1:10 (2011); Delvecchio et al. *Eur Neuropsychopharmacol.* 22(2):100-13 (2012)). These abnormalities in local brain activation also extend to functional connectivity of dorsal cortical regions and the AMG, characterized by reduced "top-down" regulatory input from cortical regions to the AMG (Zhang et al. *Neurosci Bull.* 32(3):273-85 (2016)).

MDD is also associated with alterations in resting-state functional connectivity, particularly in networks associated with cognitive control (central executive network; CEN), salience (Salience Network; SAL) and self-referential processing (default mode network; DMN) (Kaiser et al, *JAMA Psychiatry* 72: 603-611 (2015)). Compared to healthy individuals, patients with MDD show hypoconnectivity within regions of the CEN and hyperconnectivity between medial brain regions that form part of the dorsal DMN (Kaiser et al, *JAMA Psychiatry* 72: 603-611 (2015)). These changes in the internal network cohesion appear to occur in the context of reduced functional integration between resting-state networks (Kaiser et al, *JAMA Psychiatry* 72: 603-611 (2015)). Collectively, these task and resting-state abnormalities in brain functional connectivity represent the network-level correlates of the emotional dysregulation commonly observed in MDD populations.

Cognitive-Emotional Therapy

Cognitive-emotional therapy offers significant promise as a treatment intervention for MDD because of its theoretical potential to target and ameliorate neural network abnormalities. Examples of various forms of cognitive-emotional therapy include, but are not limited to, Emotional Faces Memory Task (EFMT), Wisconsin Card Sorting Test, Emotional Stroop Test, Iowa Gambling Task, Dot-probe task, Face perception task, and delay discounting task.

EFMT was developed as a cognitive-emotional training exercise that aims to enhance cognitive control for emotional information processing (and accordingly, improve emotion regulation) in MDD by targeting both cognitive control and emotional processing networks. The EFMT intervention combines working memory (N-back) and facial affect identification tasks, which have been shown to elicit activity specifically in the dorsolateral prefrontal cortex (DPFC) and AMG, respectively. EFMT prompts participants to remember the emotions observed on a series of faces, displayed one at a time on a computer screen, and subsequently indicate if the emotion observed on a given face matches the emotion shown N (number) of faces prior. The task's difficulty level (N) is calibrated based on each participant's performance to ensure a consistent challenge and engagement of the targeted neural networks. The EFMT training regimen involves manipulating emotionally salient stimuli in working memory, and participants are therefore thought to be exerting cognitive control during emotional information processing throughout task participation. A version of this task elicited simultaneous activation of the DPFC and AMG in a sample of healthy volunteers.

The Wisconsin Card Sorting Test examines abstract reasoning and the ability of a subject to problem solve in changing environments. The Wisconsin Card Sorting Test is useful for eliciting activation of the frontal lobe (e.g., prefrontal cortical regions) and is described in Chen & Sun, C. W., *Sci Rep* 7, 338 (2017); Teubner-Rhodes et al., *Neuropsychologia* 102, 95-108 (2017).

The Emotional Stroop Test is a cognitive interference task that measures the ability of a subject to process emotions when conflicting information is also presented by examining the amount of time participants take to name colors of words presented to them in the presence of an emotional distractor. The Emotional Stroop Test is useful for eliciting activation of the precentral gyms and anterior cingulate, and is described in Ben-Haim et al., *J Vis Exp.* 112 (2016); Song et al. *Sci Rep* 7, 2088 (2017).

The Iowa Gambling Task (IGT) is a decision-making task involving the complex interplay of motivational, cognitive, and response processes in choice behavior, and is useful for eliciting activation of the amygdala, and ventral-medial prefrontal cortex (vmPFC). IGT is also considered an indicator of dopamine system activity, and is described in Fukui et al. *Neuroimage* 24, 253-259 (2005) and Ono et al. *Psychiatry Res* 233, 1-8 (2015).

The Dot-probe task measures selective attention of a subject toward emotional stimuli and is useful for eliciting activation of the anterior cingulate cortex (ACC), and amygdala. The Dot-probe task is described in Gunther et al. *BMC Psychiatry* 15, 123 (2015).

The Face perception task measures the ability of a subject to understand and interpret facial expressions, and elicits activation of the fusiform face area (FFA), amygdala, and superior temporal sulcus (fSTS). See Dal Monte et al. *Nat Commun* 6, 10161 (2015); Hortensius et al. *Philos Trans R Soc Lond B Biol Sci* 371 (2016); Taubert et al. *Proc Natl Acad Sci USA* 115, 8043-8048 (2018).

The Delay discounting task evaluates the ability of a subject to set and attain goals, specifically immediate rewards vs. larger but delayed rewards. The Delay discounting task elicits activation of the orbital frontal cortex (OFC) and is described in Altamirano et al. *Alcohol Clin Exp Res* 35, 1905-1914 (2011).

Systems and Methods

Figure 8:
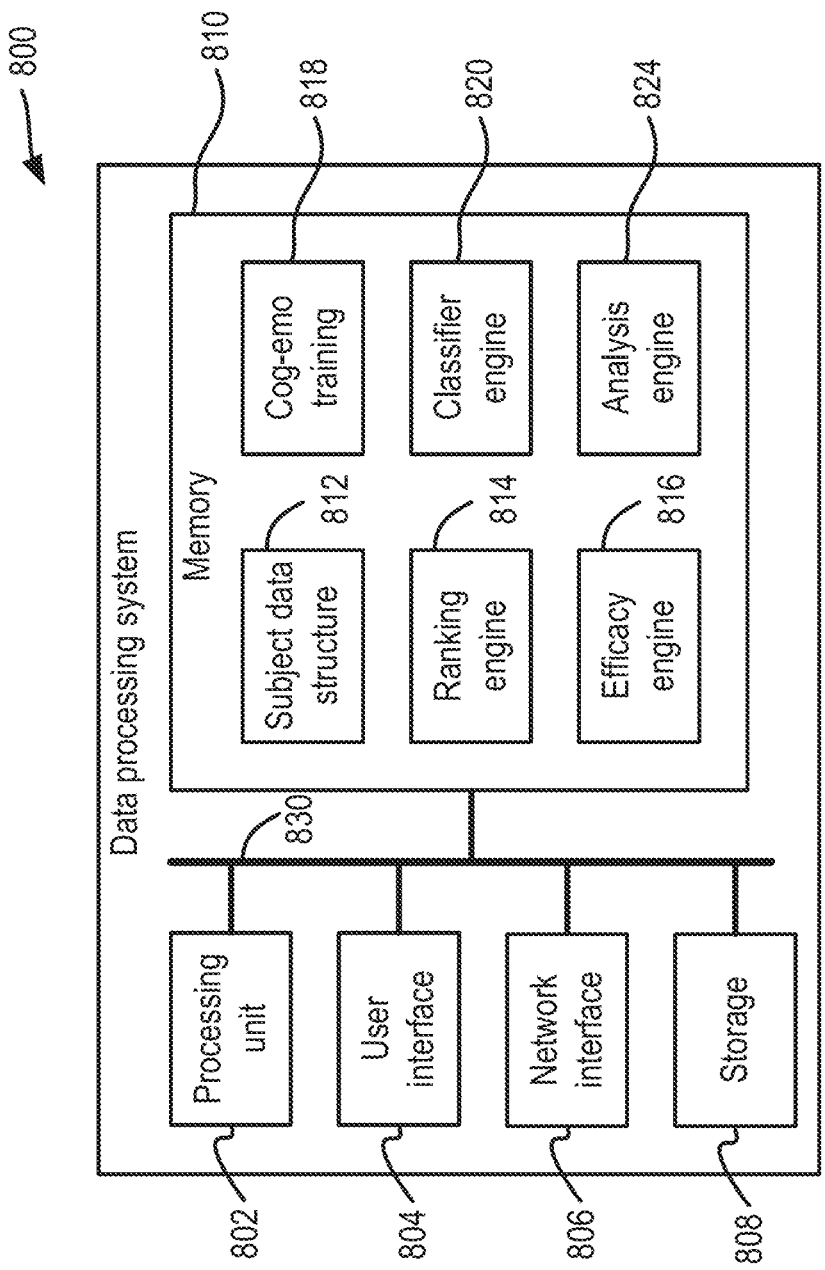
FIG. 8 shows a block diagram of an example data processing system.

FIG. 8 shows a block diagram of an example data processing system 800. The data processing system 800, can be utilized for the treatment and analysis of data related to the treatment of the affective disorder discussed above. For example, the data processing system can be utilized for administering a cognitive-emotional therapy and analyzing data associated with the therapy. The data processing system 800 can include one or more processing unit 802, a user interface 804, a network interface 806, storage 808, memory 810, and a system bus 830.

The processing unit 802 is any logic circuitry that responds to and processes instructions fetched from the memory 810. In many embodiments, the processing unit 802 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The processing unit 802 may be based on any of these processors, or any other processor capable of operating as described herein. The processing unit 802 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

The user interface 804 can include displays, input/output devices, and peripheral devices that can allow communication with one or more users. The user interface can include display devices, touch screen displays, mouse, keyboard, gesture sensitive devices, etc. the network interface 806 can allow interface with an external network, such as the Internet, an Ethernet network, or any other local or wide area network. The storage 808 can include non-volatile memory, such as, for example, a disk drive, a flash drive, a ROM, an EMPROM, an EEPROM, etc. The system bus 830 can provide communication between various components of the data processing system 800.

The memory 810 can store data and one or more software modules that the processing unit 802 can execute to perform one or more functions. Specifically, the memory 810 can include executable logic engines that can be executed by the processing unit 802. For example, the memory 810 can include a subject data structure 812, a ranking engine 814, an efficacy engine 816, a cognitive-emotional training engine 818, a classifier engine 820, and an analysis engine 824. These components of the memory 810 are discussed further below. The memory 810 can be a hardware storage device and can include volatile and/or non-volatile memory. As an example, the memory 810 can include volatile memory such as RAM, DRAM, SRAM, etc., and non-volatile memory such as those mentioned above in relation to storage 808.

FIG. 9 shows an example data structure 900. As an example, the data structure 900 can be stored in memory 810 of the data processing system 800 shown in FIG. 8. The data processing system 800 can maintain the data structure 900 to manage one or more connectivity values associated with one or more subjects. The data structure can include columns, where each column assigned a plurality of fields for storing data values. However, it is understood that any type of data structure or data structures can also be used. The data structure 900 stores key fields 902 that stores subject identifiers that identify a subject. The subject identifiers can include alphanumeric and or binary digits that can uniquely identify a subject. The data structure 900 can include keyed data corresponding to the key or subject identifier in the key fields 902. For example, the keyed data associated with a subject identifier can include the data values in rows corresponding to the subject identifier. As an example, the data structure 900 also can include fields 904 for storing data values representing a set of first connectivity values associated with one or more subject identifiers. The first connectivity values, for example, can represent a magnitude of a connection associated with at least one sub-processing region of the nervous system of the subject. In some examples, the first connectivity value can represent the magnitude measured at a first time.

The data structure 900 can further includes fields 906 for storing data values representing a rank associated with one or more of the subject identifiers. The rank can be based on the first connectivity value and can represent a position of the subject identifier in relation to first connectivity values associated with other subject identifiers. For example, the rank can represent the position of the subject identifier based on increasing first connectivity values associated with all subject identifiers. The data structure 900 can further include fields 908 for storing data values representing a classification associated with one or more subject identifiers. The classification can also be based on the first connectivity values. The classification, can for example, include a first classification value such as "eligible" and a second classification value such as "ineligible." The classification can indicate, for example, whether a subject identified by the subject identifier is eligible, or is a good candidate, for cognitive-emotional training.

The data structure 900 can further include fields 910 for storing data values representing a second connectivity value, which, like the first connectivity value, can also represent a magnitude of a connection associated with at least one sub-processing region of the nervous system of the subject. In some examples, the second connectivity value can represent the magnitude measured at a second time, such as, for example, after the subject has been exposed to the cognitive-emotional training. In some examples, the second connectivity value can represent the magnitude of a connection associated with the same at least one sub-processing region as that associated with the first connectivity value. For example, both the first and second connectivity values can represent magnitudes of connections between the DPFC and the AMG of the subjects.

The data structure 900 also can include another classification field 912 for storing data values representing efficacy associated with one or more subject identifiers. The efficacy can indicate the effectiveness of a treatment, such as, for example, the cognitive-emotional training, on the subject based on the first and the second connectivity values that are measured before and after, respectively, the administration of the treatment. The data structure 900 can include additional connectivity values, classifications, and ranks. In some examples, the data structure 900 can include values associated with connections of more than one sub-processing regions of the nervous system of the subjects. For example, the data structure can include first and/or second connectivity values measured for connections between the dACC and the AMG of the subjects.

It should be appreciated that a connectivity value can correspond to an effective connectivity, functional connectivity, or integration across at least one sub-processing region of the nervous system of a subject. In some embodiments, the connectivity values can be determined from a device configured to perform an fMRI on a subject. In some embodiments, the connectivity values can be inferred from one or more outputs provided by fMRI. It should be appreciated that the connectivity values can be inferred or identified from any device that is configured to determine effective connectivity, functional connectivity, or integration across at least one sub-processing regions.

Figure 10:
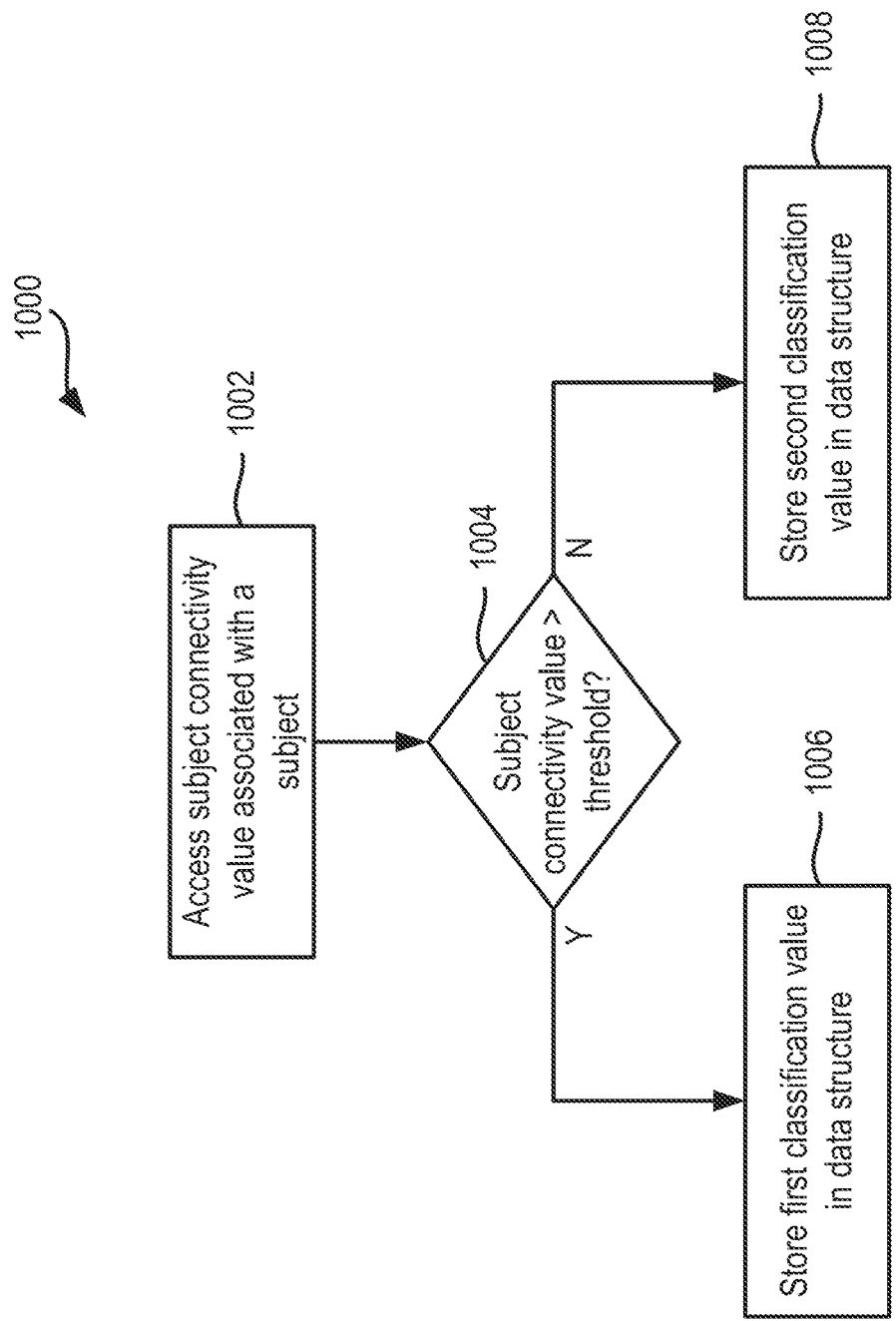
FIG. 10 shows a flow diagram of an example process representing a classifier engine of the data processing system shown in FIG. 8 that can be utilized to determine an eligibility of subjects for a treatment.

FIG. 10 shows a flow diagram of an example process 1000 representing a classifier engine 820 that can be utilized to determine an eligibility of subjects for a treatment. In particular, the flow diagram 1000 can be utilized to update the data structure 900 with classification values that indicate whether the associate subject is eligible or ineligible for the treatment, such as, for example, a cognitive-emotional training. The process 1000 includes accessing a subject connectivity value associated with a subject (1002). In particular, the process 1000 can include accessing a data structure including a subject identifier identifying a subject and a subject connectivity value derived from at least one of a scan or test provided to the subject, where the subject connectivity value represents a magnitude of a connection associated with at least one sub-processing region of a nervous system of the subject. The data structure, for example, can be the data structure 900 shown in FIG. 9. The subject connectivity value can represent, for example, the first or the second connectivity values in the data structure 900. The at least one sub-processing region of the nervous system can include at least one of, without limitation, the DPFC, the AMG, the dACC, the DMN, the SAL, the LCEN, the RCEN, the dDMN, and the vDMN. As an example, the data processing system 800 can access the first connectivity value 10 from the data structure 900 associated with the subject identified by the subject identifier "Subject 1."

The process 1000 executing executable logic that includes comparisons rules, execution of which compares the subject connectivity value to a threshold value (1004). In particular, the process 1000 can include comparing, by the data processing system, the subject connectivity value to a connectivity threshold value to determine a classification of the subject. As an example, the data processing system 800 can store the connectivity threshold value in memory 810, and can compare, for example, the first connectivity value of 10 stored in the data structure 900 to the threshold value. The threshold value can represent a baseline number that can be based on the measurement environment and setup to which the subject is exposed, and can vary based on the changes in the measurement environment or setup. For example, different measuring instruments on the same subjects may generate different connectivity values. Therefore, the threshold value can be selected based on the measurement environment and setup.

The process 1000 includes storing a first classification value in the data structure if the subject connectivity value is greater than the threshold (1006). In particular, the data processing system 800, responsive to determining that the subject connectivity value exceeds the connectivity threshold value, stores in the data structure an association between the subject identifier and a first classification value corresponding to a first classification. As an example, the first classification can represent ineligibility, and the first classification value can include the entry "Ineligible." For example, referring to the data structure 900 shown in FIG. 9, the data processing system 800 can compare the first connectivity value of 6 of Subject 2 to an example threshold value of 5, and store the entry "Ineligible" in the classification column (field 908) of the data structure 900 in association with the subject identifier "Subject 2."

The process 1000 includes storing a second classification value in the data structure if the subject connectivity value is less than the threshold (1006). In particular, the data processing system responsive to determining that the subject connectivity value is less than the connectivity threshold value, store in the data structure an association between the subject identifier and a second classification value corresponding to a second classification. As an example, the second classification can represent eligibility, and the second classification value can include the entry "Eligible." For example, in the data structure 900, the data processing system can compare the first connectivity value of 15 of the Subject 3 with a threshold value of 20 and store the entry "Eligible" in the classification column (field 908) of the data structure 900 in association with the subject identifier "Subject 3."

The process 1000 may also be executed iteratively, updating the data structure 900 as new connectivity values are received. Thus, the process 1000 may update the field 908 with the appropriate first or second classification value based on changes in the subject connectivity values in relation to the connectivity threshold.

In some examples, the sub-processing regions can include the dorsolateral prefrontal cortex (DPFC) and the amygdala (AMG), and the connectivity value and the connectivity threshold value represent an effective connectivity between the DPFC and the AMG and an effective connectivity threshold value between the DPFC and the AMG. The first classification value can indicate that the subject is ineligible, and the second classification value indicates that the subject is eligible. That is, if the effective connectivity value is less than a threshold value, the associate subject is eligible for the cognitive-emotional training, and the data structure 900 can be accordingly updated.

In some examples, the sub-processing regions can include the anterior cingulate cortex (dACC) and the amygdala (AMG), and the connectivity value and the connectivity threshold value represent an effective connectivity between the dACC and the AMG and an effective connectivity threshold value between the dACC and the AMG. The first classification value can indicate that the subject is eligible, and the second classification value indicates that the subject is ineligible. That is, if the effective connectivity value is greater than a threshold value, the associate subject is eligible for the cognitive-emotional training, and the data structure 900 can be accordingly updated.

In some examples, the sub-processing regions can include the default mode resting state network (DMN), and the connectivity value and the connectivity threshold value represent a functional connectivity within the DMN and a functional connectivity threshold value associated with the DMN. The first classification value can indicate that the subject is eligible, and the second classification value indicates that the subject is ineligible. That is, if the functional connectivity value is greater than a threshold value, the associate subject is eligible for the cognitive-emotional training, and the data structure 900 can be accordingly updated.

In some examples, the sub-processing regions can include the default mode resting state network (DMN) or the salience resting state network (SAL), and the connectivity value and the connectivity threshold value represent a functional connectivity within the DMN or SAL and a functional connectivity threshold value associated with the DMN or SAL. The first classification value can indicate that the subject is eligible, and the second classification value indicates that the subject is ineligible. That is, if the functional connectivity value is greater than a threshold value, the associate subject is eligible for the cognitive-emotional training, and the data structure 900 can be accordingly updated.

In some examples, the sub-processing regions can include one of LCEN and RCEN, dDMN and vDMN, LCEN and vDMN, and LCEN and SEL. The connectivity value and the connectivity threshold value, respectively, represent an integration between the selected pair of sub-processing regions. The first classification value indicates that the subject is ineligible, and the second classification value indicates that the subject is eligible. That is, if the integration value is less than a threshold value (for example, a threshold value of 0), the associate subject is eligible for the cognitive-emotional training, and the data structure 900 can be accordingly updated.

In some examples, the classifier 820 engine can consider connectivity values between or within more than one set of sub-processing regions to determine the eligibility of the subject. For example, the classifier engine 820 can consider a combination of the effective connectivity between the DPFC and the AMG and the dACC and the AMG to determine eligibility. If the effective connectivity between DPFC and the AMG is less than a threshold, and the effective connectivity between the dACC and the AMG is above a threshold, the classifier engine 820 can determine that the subject is eligible, and update the data structure 900 accordingly.

Figure 11:
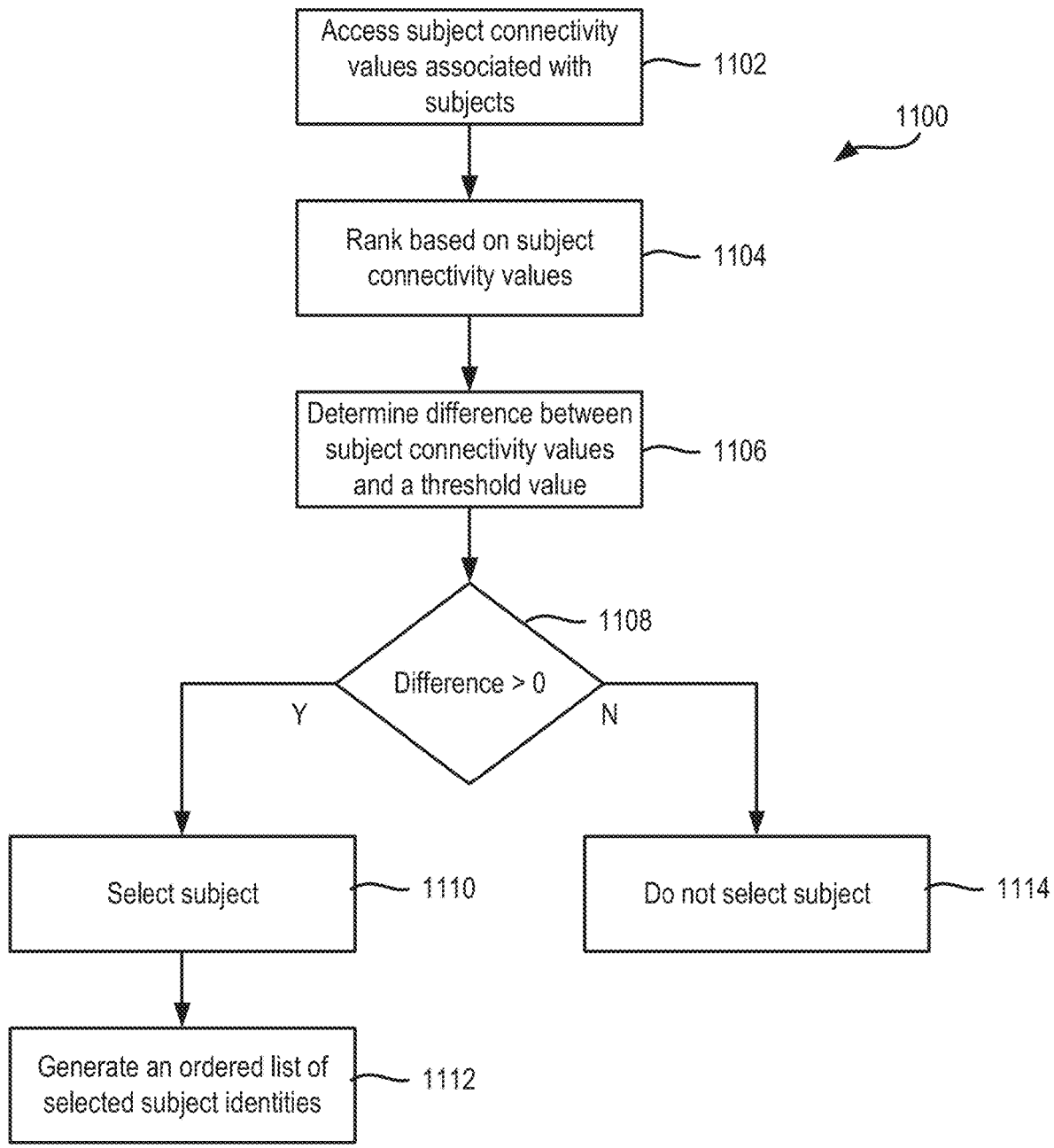
FIG. 11 shows a flow diagram of an example process representing a ranking engine of the data processing system shown in FIG. 8 that can be utilized to rank subjects based on their respective measured subject connectivity values.

FIG. 11 shows a flow diagram of an example process 1100 representing a ranking engine 814 of the data processing system 800 shown in FIG. 8 that can be utilized to rank subjects based on their respective measured subject connectivity values. The process 1100 can include accessing subject connectivity values associated with subjects (1102). In particular, the process 1100 can include identifying from a data structure a plurality of subject connectivity values associated with a plurality of subject identifiers corresponding to a plurality of subjects, where each subject connectivity value in the plurality of subject connectivity values represents a magnitude of a connection associated with at least one sub-processing region of a nervous system of a respective subject of the plurality of subjects. For example, the ranking engine 814 can access the plurality of first connectivity values listed in the data structure 900 associated with the plurality of subject identifiers "Subject 1" to "Subject n."

The process 1100 includes ranking based on the connectivity values (1102). In particular, the process 1100 can include assigning to each subject identifier in the data structure a rank based on the subject connectivity value. For example, referring to the data structure 900 in FIG. 9, the ranking engine 814 can assign ranks in the rank column based on increasing first connectivity values, with the lowest connectivity value being assigned the lowest rank and the highest connectivity value being assigned the highest rank. The ranking may in some instances be can be assigned in the reverse order.

The process 1100 can include determining the difference between subject connectivity values and a threshold value (1106). In particular, the ranking engine 814 can determine the difference between the first connectivity values shown in FIG. 9 and a threshold value. In some instances, the threshold value can be similar to that selected by the classifier engine 820 discussed above. The process 1100 includes determining whether the difference is greater than 0 (1108). That is, whether the connectivity value is greater than or equal to the threshold value.

The process 1100 includes selecting a subset of subjects, each subject of the subset selected based on a difference between the connectivity threshold value and the subject connectivity value (1110). As an example, the ranking engine 814 can select m subjects having the m highest differences between their connectivity values and the threshold value. Once the subjects are selected, the ranking engine 814 can generate an ordered list of the selected subject identities based on the respective ranks (1112).

The process 1100 may also be executed iteratively, updating the data structure 900 as new connectivity values are received. Thus, the process 1000 may update the field 906 with the appropriate ranks based on received first connectivity values of additional subjects, or based on new first connectivity values associated with existing subject identifiers in the data structure 900.

In some examples, the at least one sub-processing region can include the DPFC and the AMG or the dACC and the AMG, and the subject connectivity values can represent the effective connectivity between the sub-processing engine. For DPFC and AMG, the subject connectivity values associated with the selected subset of subjects are below the connectivity threshold value. For dACC and AMG, the subject connectivity values associated with the selected subset of subjects are above the connectivity threshold value.

In some examples, the at least one sub-processing regions can be the dDMN or the SAL, and the subject connectivity values can represent functional connectivity within the DMN or the SAL. In some such examples, subject connectivity values associated with the selected subset of subjects are above the connectivity threshold value.

In some examples, a pair of sub-processing regions can be the LCEN and the RCEN, the dDMN and the vDMN, the LCEN and the vDMN, or the LCEN and the SAL. The subject connectivity values can represent functional connectivity within the pair of sub-processing regions. In some such examples, the subject connectivity values associated with the selected subset of subjects are above the connectivity threshold value.

The process 1100 can also include not selecting the subject that have a connectivity value that is less than the threshold value. In some instances, this can remove candidate that are not predisposed to respond to the treatment, such as the cognitive-emotional training. Therefore, by eliminating those subjects from the overall list of subjects can improve the time for carrying out the treatment.

Figure 12:
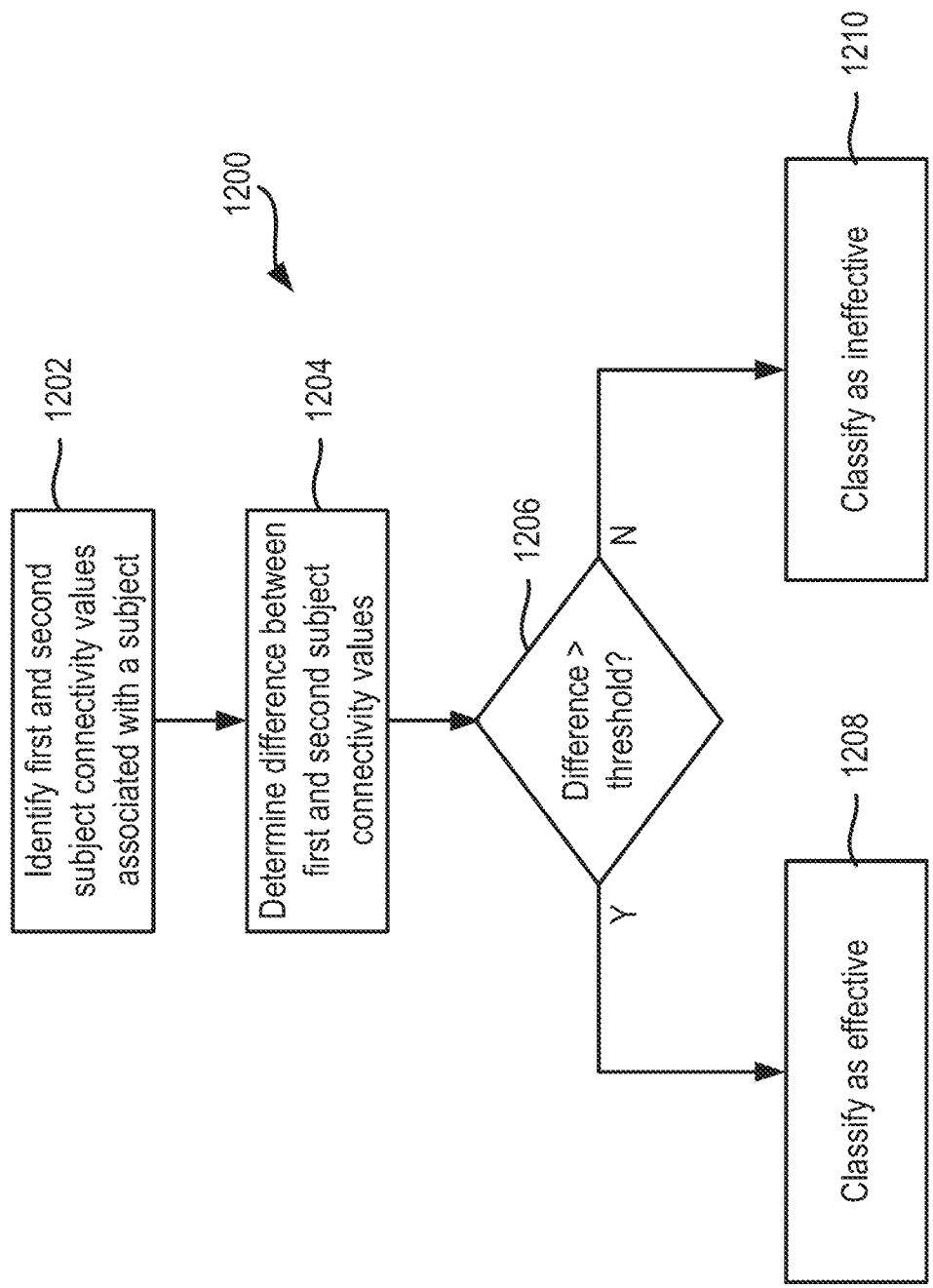
FIG. 12 shows a flow diagram of an example process representing an efficacy engine of the data processing system shown in FIG. 8 that can be utilized to determine the efficacy of a cognitive-emotional training on a subject.

FIG. 12 shows a flow diagram of an example process 1200 representing an efficacy engine 816 shown in FIG. 8 that can be utilized to determine the efficacy of a cognitive-emotional training on a subject. The process 1200 includes identifying first and second connectivity values associated with a subject (1202). In particular, the efficacy engine 816 identify a first connectivity value of a subject, where the first connectivity value represents a first magnitude of a connection associated with at least one sub-processing region of a nervous system of a subject at a first time, and a second connectivity value of the subject, where the second connectivity value represents a second magnitude of the connection associated with the at least one sub-processing region of the nervous system of the subject at a second time after the subject has been exposed to cognitive-emotional training. For example, referring to FIG. 9, the efficacy engine 816 can access the data structure 900 to identify the first and second connectivity values for a subject, such as those associated with the subject identity: "Subject 1."

The process 1200 includes determining a difference between the first connectivity value and the second connectivity values (1204). For example, the efficacy engine 816, for "Subject 1" can determine the difference between the first and second connectivity values as being equal to 10.

The process 1200 includes determining whether the difference is less than or greater than a threshold value (1206). In particular, the efficacy engine 816 can access a stored value or an operator provided threshold value. The threshold value can represent the minimum difference in the connectivity values that should be observed to indicate that there is an effective improvement in the subject as a result of the treatment.

The process 1200 includes classifying the subject as effective if the difference is greater than the threshold (1208) and classifying the subject as ineffective if the difference is less than the threshold (1210). In particular, the efficacy engine 816 responsive to determining that the difference exceeds a threshold value, store in the data structure an association between the subject identifier and a first classification value corresponding to a first classification. As an example, the first classification can be effectiveness, and the first classification value can be the entry "Y." Further, the efficacy engine 816 responsive to determining that the difference is less than the threshold value can store in the data structure an association between the subject identifier and a second classification value corresponding to a second classification. For example, the second classification can be ineffectiveness, and the second classification value can be the entry "N." It is understood that other entries other than "Y" and "N" can also be used.

The process 1200 may also be executed iteratively, updating the data structure 900 as new connectivity values are received. Thus, the process 1000 may update the field 912 with the appropriate entry based on changes in the first and/or second connectivity values, or based on new first and second connectivity values in new keyed data associated with new subject identifiers.

In some examples, the sub-processing regions can include the DPFC and the AMG or the dACC and the AMG. The first connectivity value and the second connectivity value represent an effective connectivity between the DPFC and the AMG or the dACC and the AMG of the subject. In some examples, the sub-processing regions can include the dDMN or the SAL. The first connectivity value and the second connectivity value represent a functional connectivity within the dDMN or the SAL of the subject. In some examples, the sub-processing regions can include the pairs LCEN and RCEN, the dDMN and the vDMN, the LCEN and the vDMN, or the LCEN and the SAL. The first connectivity value and the second connectivity value represent an integration across the particular pair of sub-processing regions of the subject.

In some examples, the analysis engine 824 can carry out analysis of the data collected before, during, or after the treatment. For example, the analysis engine 824 can perform data analysis such as Neuroimaging Preprocessing and Quality Assurance, Resting State Network Connectivity Analysis, Task-based fMRI (Connectivity) Analysis, Statistical Analysis, analyzing changes in resting-state functional connectivity, effective connectivity, and integration in post-treatment data discussed above. In some examples, the analysis engine can perform analysis of neuroimaging data to determine the effective connectivity, functional connectivity, and the integration values. As an example, the analysis engine 824 can include software based on the procedure discussed in Anand, A., Li, Y., Wang, Y., Wu, J., Gao, S., Bukhari, L., Mathews, V. P., Kalnin, A., and Lowe, M. J. (2005). Activity and connectivity of brain mood regulating circuit in depression: a functional magnetic resonance study. Biol Psychiatry 57, 1079-1088, and Raichle, M. E., MacLeod, A. M., Snyder, A. Z., Powers, W. J., Gusnard, D. A., and Shulman, G. L. (2001). A default mode of brain function. Proc Natl Acad Sci USA 98, 676-682.

In some examples, the cog-emo training engine 818 can perform one or more cognitive-emotional therapies such as, for example, EFMT, the Wisconsin card sorting test, the emotional stroop test, the Iowa gambling task, the dot probe task, the face perception task and the delay discounting task, discussed above.

System

The system can include any script, file, program, application, set of instructions, or computer-executable code, that is configured to enable a computing device to administer emotion identification and working memory tasks to users. The computing device can include or be connected with a display. The computing device can be a laptop, desktop computer, mobile phone, tablet, or other computing device. The system can include a database that includes a plurality of faces images. The faces illustrated by the face images can be in different emotional states, e.g., happy, sad, scared, excited, etc. Each of the face images can be labeled in the database with its corresponding emotional state. In some implementations, the face images can be generated on demand using a reference data base that includes portions of face images in different emotional states. For example, a face image in a happy state can be divided into sub-images that include only a single facial component, such as the eyes, mouth, etc. The system can combine the sub-images into unique face images on demand. The system can also include a plurality of training policies in the database. The training policies can control for how long each of the images are presented to a user and in what order.

The system can present a series of images to the user. During a test with the system, participants identify the emotions that they observe on a series of images of faces that are presented one at a time on a display. Each of the images can be displayed for about 1 second, followed by a fixation cross for 1 second. As the images are presented to the user, the system can instruct the user to remember the sequence of emotions that they observed. Using an N-back working memory paradigm, participants are prompted to indicate after each presented face whether the emotion on the face they just observed is the same as the emotion that was shown N faces prior. In some implementations, the training policy can indicate that each training session contains 15 blocks of the task during which the N level varies depending on the participant's performance: the difficulty level increases or decreases across blocks as a participant's accuracy improves or declines (respectively). The first training session begins with a difficulty level of N=1 and the starting difficulty level for subsequent sessions is determined by performance at the prior session. Because EFMT utilizes a progressively challenging working memory paradigm, the task is tailored to a participant's ability level and ensures a consistent challenge throughout each training session. N-back working memory tasks that are progressively challenging have been shown to improve working memory performance.

EXAMPLES

The present technology is further illustrated by the following Examples, which should not be construed as limiting in any way.

Example 1: Experimental Materials and Methods

Subjects. 25 un-medicated MDD participants experiencing a current major depressive episode (MDE) were recruited to participate in a study protocol which involved an fMRI scan before and after completing six weeks of emotional faces memory task (EFMT) or sham-control training (CT) as part of a parent clinical trial protocol (NCT01934491). Participants were recruited online and through advertisements in local newspapers for depression research studies. All participants were between the ages of 18-55 and were evaluated by trained clinicians using the Structured Clinical Interview for DSM-IV-TR Axis I Disorders (SCID) (see First, M. B. et al. *Structured clinical interview for DSM-IV axis disorders (SCID)* (New York State Psychiatric Institute, Biometrics Research, New York, NY (1995)). Other Axis I comorbid diagnoses (excluding psychotic disorders, bipolar disorders and substance abuse or dependence within the past six months) were permitted as long as the participants' MDD diagnosis was considered to be primary. MDD severity, as measured by the Hamilton Depression Rating Scale—17-item version (Ham-D) (see Hamilton, J. P et al. *Am J Psychiatry* 169:693-703 (1960)), had to be at least "moderate" (Ham-D≥16). Participants with very severe MDD (Ham-D≥27) were excluded from the study and referred for treatment. Participants who reported taking any antidepressant medications during their current MDE, as well as those with a history of treatment non-response (2+ failures of an adequate trial of a standard antidepressant medication) were excluded from the study. Cognitive-behavioral therapy attendance in the six weeks prior to, or at any time during, the study was also exclusionary as per the protocol. Participants with visual or motor impairments that were thought to interfere with performance on the EFMT training were also excluded.

After an initial pre-screening interview, potentially eligible participants were informed about the study procedures who then signed informed consent forms to complete screening and baseline procedures. Participants who were eligible for and enrolled in the parent clinical trial investigating EFMT efficacy were subsequently offered enrollment in the fMRI study protocol, and provided informed consent if they elected to participate. Participants were reimbursed for each study session completed to compensate for time and travel expenses.

Procedures. The study intervention (EFMT) was administered over 20 separate research visits. At the first visit, the SCID and Ham-D were administered to the subjects to confirm MDD diagnosis and determine symptom severity. A subsequent baseline evaluation was conducted which included the pre-treatment fMRI scan. Participants were randomly assigned to the EFMT or CT groups by a research coordinator using a pre-determined randomization sequence for group assignment. Participants were assigned to complete 18 training sessions over 6 weeks (an approximate duration of 20-35 minutes each, three times per week). Participants that failed to complete at least 2 training sessions in any week, or that missed greater than 3 training sessions during the course of the study, were discontinued as per the clinical trial protocol. Weekly depression severity (Ham-D) assessments were conducted by PhD or MD-level clinicians who were blind to participant group assignment. Ham-D raters were extensively trained to administer the assessment and demonstrated an intra-class correlation coefficient (ICC) of >0.8 on two separate training interviews. An outcome evaluation was conducted within 1 week of completing the training sessions, at which time baseline assessments and the fMRI scanning procedures were repeated.

Cognitive Training Interventions. EFMT has been fully described in previous publications (see Iacoviello, B. M. et al. *Eur Psychiatry* 30:75-81 (2015); Iacoviello, B. M. et al. *Depress Anxiety* 31:699-706 (2014)). EFMT was designed to enhance cognitive control for emotional information processing in MDD by targeting both cognitive control and emotional processing networks, and was accomplished by combining emotion identification and working memory tasks. In the EFMT task, participants were asked to identify the emotions that they observed on a series of pictures of faces that were presented one at a time on a computer screen, and subsequently remember the sequence of emotions that they observed. FIG. 1 depicts an example trial sequence in the EFMT task. Using an N-back working memory paradigm, participants were prompted to indicate after each presented face whether the emotion on the face they had just observed was the same as the emotion that was shown N faces prior. Thus, the EFMT task involved exerting cognitive control over emotional information processing and was hypothesized to induce simultaneous activation of the amygdala (AMG) and the dorsolateral prefrontal cortex (DPFC). The CT condition involved a working memory training exercise which utilized the same N-back paradigm as EFMT, but included neutral shapes as stimuli instead of emotional faces. A session of EFMT or CT would take approximately 15-25 minutes to complete, and the study regimen involved completing 18 sessions of EFMT or CT over a 6 week period (3 sessions per week for 6 weeks).

Neuroimaging Data Acquisition. Imaging data were acquired at ISMMS on a 3T Skyra scanner (Siemens, Erlangen, Germany) with a 32 channel receiver coil. Participants were scanned at study enrollment (baseline) and immediately after completing six weeks of EFMT training. Anatomical as well as resting-state and task-based fMRI data were acquired. The task included an abridged and modified version of an EFMT session. Twelve blocks of 10 trials began with a 2.5 s cue identifying the target type (0-back, 1-back, or 2-back). In 0-back trials, subjects viewed a target image (a face depicting an emotion) and indicated if each subsequent stimulus was exactly the same image as the target image. In the 1-back and 2-back trials, participants indicated whether or not each face depicted the same emotion as that presented either "1-back" or "2-back." The anatomical, resting-state and task acquisitions were identical at baseline and post-treatment for all participants.

The resting-state and task-fMRI data were acquired using a T2* single shot echo planar gradient echo imaging sequence with the following parameters: time to echo/ repetition time (TE/TR)=35/1000 millisecond (ms), 2.1 mm isotropic resolution, 70 contiguous axial slices for whole brain coverage, field of view (FOV): 206×181×147 mm$^3$, matrix size: 96×84, 60 degrees flip-angle, multiband (MB) factor 7, blipped CAIPIRINHA (Controlled Aliasing in Parallel Imaging Results in Higher Acceleration) phase-encoding shift=FOV/3, ~2 kHz/Pixel bandwidth with ramp sampling, echo spacing: 0.68 ms, and echo train length 57.1 ms. The duration of the resting-state acquisition was 10 minutes and the duration of the WM task was 7 minutes and 34 seconds. Structural images were acquired using a T1-weighted, 3D magnetization-prepared rapid gradient-echo (MPRAGE) sequence (FOV: 256×256×179 mm$^3$, matrix size: 320×320, 0.8 mm isotropic resolution, TE/TR=2.07/2400 ms, inversion time (TI)=1000 ms, 8 degrees flip-angle with binomial (1, −1) fat saturation, bandwidth 240 Hz/Pixel, echo spacing 7.6 ms, in-plane acceleration (GeneRalized Autocalibrating Partial Parallel Acquisition) factor 2 and total acquisition time of 7 min).

Neuroimaging Preprocessing and Quality Assurance. Task and resting-state fMRI (rs-fMRI) data acquired at baseline and post-treatment were preprocessed separately using identical methods. All analyses were implemented using the Statistical Parametric Mapping software, version 12 (SPM12; www.fil.ion.ucl.ac.uk/spm/software/spm12/) and the Data Processing and Analysis for Brain Imaging Toolbox (see Yan, C. G. et al. *Neuroinformatics* 14:339-351 (2016)). Each fMRI dataset was motion corrected to the first volume with rigid-body alignment; coregistration between the functional scans and the anatomical T1 scan; spatial normalization of the functional images into Montreal Neurological Institute stereotaxic standard space; spatial smoothing within functional mask with a 6-mm at full-width at half-maximum Gaussian kernel. Resting-state data were additionally preprocessed to correct for head motion using the following steps: wavelet despiking (removing signal transients related to small amplitude (<1 mm) head movements) (see Patel, A. X. et al. *Neuroimage* 95:287-304 (2014)); detrending; and multiple regression of motion parameters and their derivatives (24-parameter model) (see Friston, K. J. et al. *Magn. Reson. Med.* 35:346-355 (1996)) as well as white matter (WM), cerebro-spinal fluid (CSF) time series and their linear trends. The WM and CSF signals were computed using a component-based noise reduction method (CompCor, 5 principal components) (see Behzadi, Y. et al. *Neuroimage* 37:90-101 (2007)). Lastly, a bandpass filtering was applied ([0.01-0.1] Hz). Individual task-fMRI and rs-fMRI datasets were excluded if volume-to-volume head motion was above 3 mm or 1 degree. No significant differences were present in maximal or mean head motion between baseline and follow-up scans (all p>0.2).

Figure 2A:
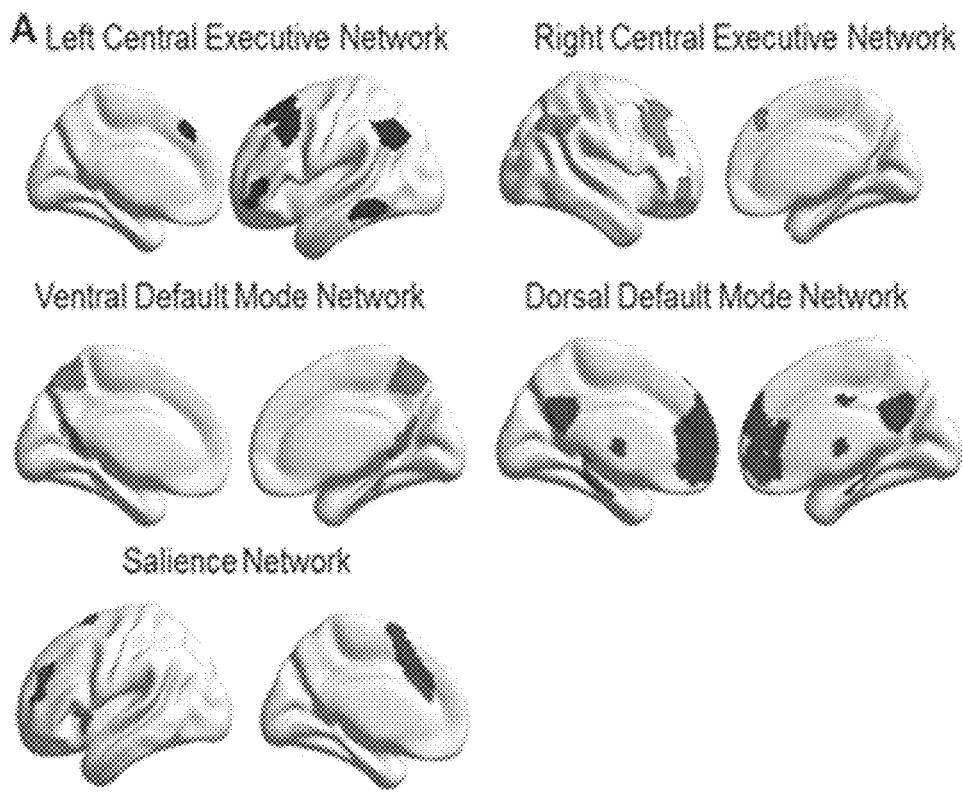
FIGS. 2A-2B illustrate resting-state functional connectivity.

Resting State Network Connectivity Analysis. rs-fMRI data acquired at baseline and post-treatment were analyzed separately using identical methods as described below. The strategy implemented focused on the resting-state networks that were most relevant to MDD. Specifically, connectivity of the ventral (vDMN) and dorsal (dDMN) default mode network, the left (LCEN) and right (RCEN) central executive network and the salience network (SAL) were examined (FIG. 2A). To ensure the reproducibility of the analyses, these networks were defined using validated and freely available templates provided by the Functional Imaging in Neuropsychiatry Disorders Lab, Stanford University (<http://findlab.stanford.edu/functional_ROIs.html>) (see Shirer, W. R. et al. *Cerebral Cortex* 22:158-165 (2012)). In each participant, the within-network and between-network functional connectivity was calculated for each network that respectively reflect functional cohesiveness and segregation. For the within-network functional connectivity, the average voxelwise time series within each network region was computed, and then the pairwise Pearson's correlations between network regions was calculated and averaged. For the between-network functional connectivity, an average time-series within each network (averaging all the time-series of the voxels part of the network) was first calculated and then the Pearson's correlation between each pair of networks' time-series was computed. Both within-network and between-network measures were further Fisher Z-transformed.

Task-based fMRI (Connectivity) Analysis. Task-fMRI data acquired at baseline and post-treatment were analyzed separately using identical methods as described below. Herein, the focus was on effective connectivity computed using Dynamic Causal Modeling (DCM; see Friston, K. J. et al. *Neuroimage* 19:1273-1302 (2003)). In DCM, the endogenous connections represented task-independent coupling strengths between regions while the modulatory effects represented task-induced alterations in inter-regional connectivity (Id.). The modeled neuronal dynamics were then related to observed blood oxygen level-dependent (BOLD) signal using a hemodynamic forward model (see Stephan, K. E. et al. *Neuroimage* 38:387-401 (2007)). Following established procedures (see Dima, D. et al. *Human Brain Mapping* 36:4158-4163 (2015); Dima, D. et al. *Transl. Psychiatry* 6:e706 (2016); Moser, D. A. et al. *Mol. Psychiatry* 23:1974-1980 (2018)), spherical 5-mm volumes of interest (VOIs) were defined bilaterally, centered on the MNI coordinates of the group maxima of the working memory load-dependent modulation at baseline: Left inferior parietal cortex (PAR): −42,−48,44, right PAR: 44,−38, 42; dACC left dorsal anterior cingulate cortex (dACC): −6 24 44, right dACC: 6 22 44; left DPFC: −28 4 60, right DPFC: 28 8 58; left AMG: −26 −4 −20, right AMG: 26 −2 −20). The same VOIs were used in the post-treatment DCM to ensure continuity between analyses. Regional time series were summarized with the first eigenvariate of all activated (at p<0.01) voxels within the participant-specific VOIs. The VOIs defined above were used to specify the basic 8-region DCM in all participants. Reciprocal connections were defined between these regions both within and between hemispheres. The effect of working-memory load (driving input) entered the PAR bilaterally. Starting from this basic layout, a structured model space was derived by considering the modulatory effect of working-memory load on the inter-regional coupling strength. Random effects Bayesian Model Averaging (BMA) was then conducted to obtain average connectivity estimates across all models for each participant (see Penny, W. D. et al. *PLoS Comput Biol* 6:e1000709 (2010); Stephan, K. E. et al. *Neuroimage* 49:3099-3109 (2010)) as BMA accommodates uncertainty about models when estimating the consistency and strength of connections. The resulting posterior means from the averaged DCM from the baseline and post-treatment datasets were used to test for changes in the modulatory effects of working-memory load on inter-regional connectivity. For completeness, differences between baseline and post-treatment in working memory load-dependent modulation of brain activity were examined using general linear models and are reported in FIG. 4.

Statistical Analysis Strategy. Effect sizes for repeated measures based on Cohen's d were computed to estimate the post-treatment changes of any given functional measure using equation (1):

$$d = \frac{m1 - m2}{s * \sqrt{2(1-r)}} \quad (1)$$

wherein m1 and m2 are the average value of a given measure at baseline and at post-treatment respectively; s is the average standard-deviation of a given measure at baseline and post-treatment, and r is the value of a given connectivity measure between baseline and post-treatment. Only results with an effect size greater than 0.3 were reported as these were more likely to be meaningful based on the conventional interpretation of Cohen's d (see Cohen, J. *Statistical power and analysis for the behavioral sciences*. Hillsdale, N.J., Lawrence Erlbaum Associates, Inc., (1988)). Pearson's correlations were used to assess the relationship between change in level of symptoms and change in brain imaging measures. Given the exploratory nature of the study the threshold of statistical inference was p<0.05, uncorrected. Comparison of different clinical measures between baseline and post-treatment scans was based on paired t-tests.

Example 2: Post-Treatment Observations in Resting-State Functional Connectivity and Effective Connectivity Twenty-five participants provided signed consent to participate in the present study. Two participants received baseline fMRI scans but were discontinued from the parent clinical trial protocol prior to randomization. Sixteen of these participants had been assigned to the EFMT condition in the parent clinical trial, and seven participants were assigned to the control (CT) condition. Five participants were lost to attrition and did not complete the clinical trial protocol or outcome fMRI scan (two participants in the EFMT group and three participants in the CT group). The current study sample included fourteen participants that completed the EFMT regimen, for whom valid pre-post fMRI and behavioral data were available. Four sham-control participants also had valid pre-post imaging and behavioral data. The current report includes the fourteen EFMT participants with valid pre-post imaging and behavioral data. FIG. 5 provides the demographic and clinical characteristics of the fourteen EFMT-treated MDD participants in the study.

In the parent clinical trial, from which participants in the current study were derived, EFMT was observed to result in significantly superior MDD symptom reduction from baseline to study outcome compared to CT (see Iacoviello, B. M. et al. *npj Digital Medicine* 1:21 (2018)). The fourteen participants in the present sample also demonstrated, on average, a clinical response to the EFMT intervention (Ham-D improvement from a mean score of 19.14 (SD=2.6) at baseline to a mean score of 11.43 (SD=5.12) at study outcome; t(13)=6.88, p<0.001) (FIG. 5).

Figure 2B:
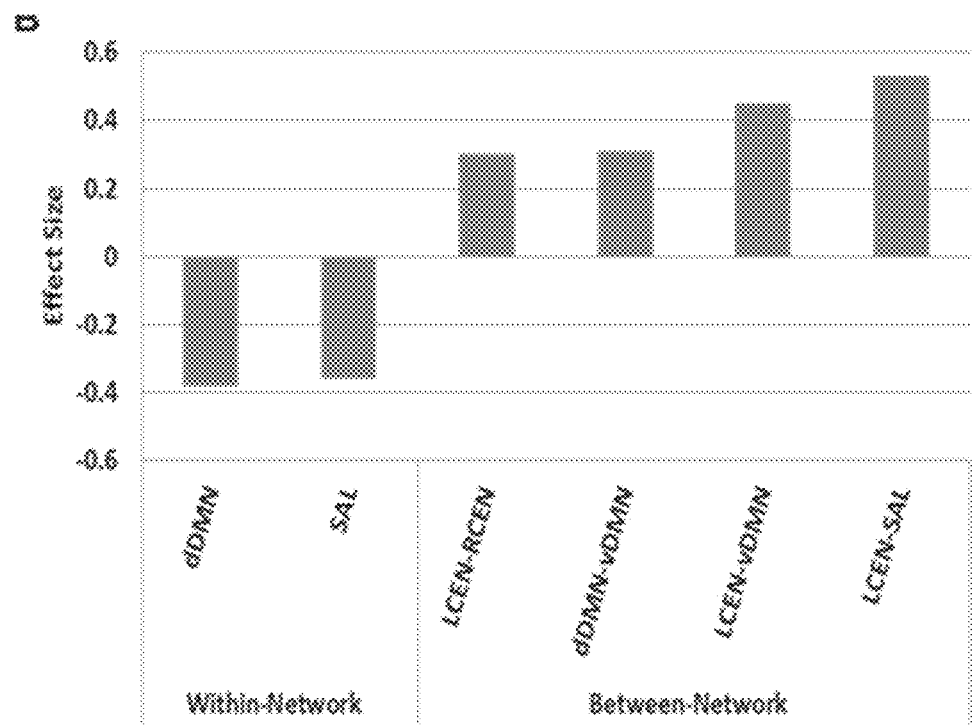

Changes in resting-state functional connectivity. As shown in FIG. 2B, post-treatment reductions were observed in within-network connectivity in the dDMN (d=−0.38) and SAL (d=−0.36). By contrast, connectivity was increased between the LCEN and RCEN (d=0.30), between the vDMN and dDMN (d=0.32), and between the LCEN and both vDMN (d=0.45) and SAL (d=0.53) (FIG. 2B). However, correlations between changes in resting-state connectivity and symptomatic change post-treatment were generally low and did not achieve statistical significance.

Figure 3A:
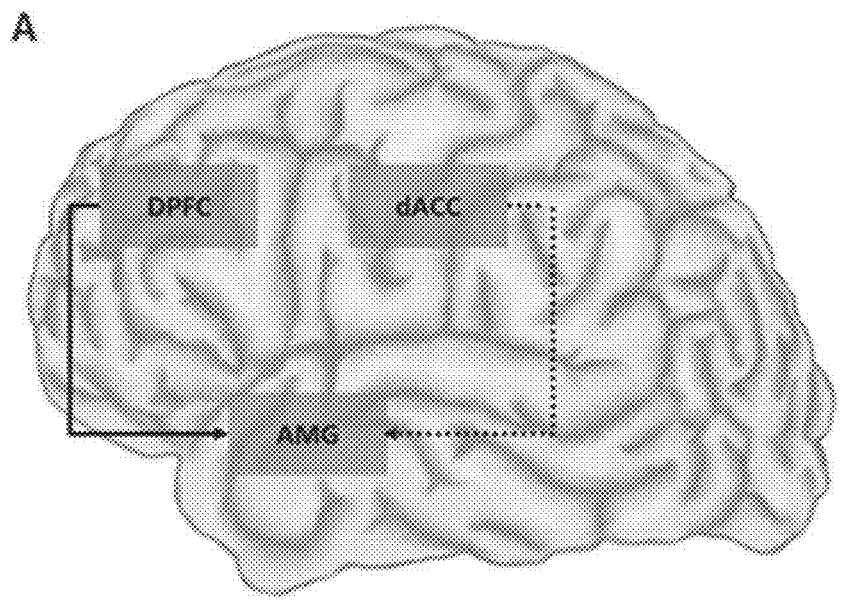
FIGS. 3A-3B illustrate effective connectivity during the EFMT task.
Figure 3B:
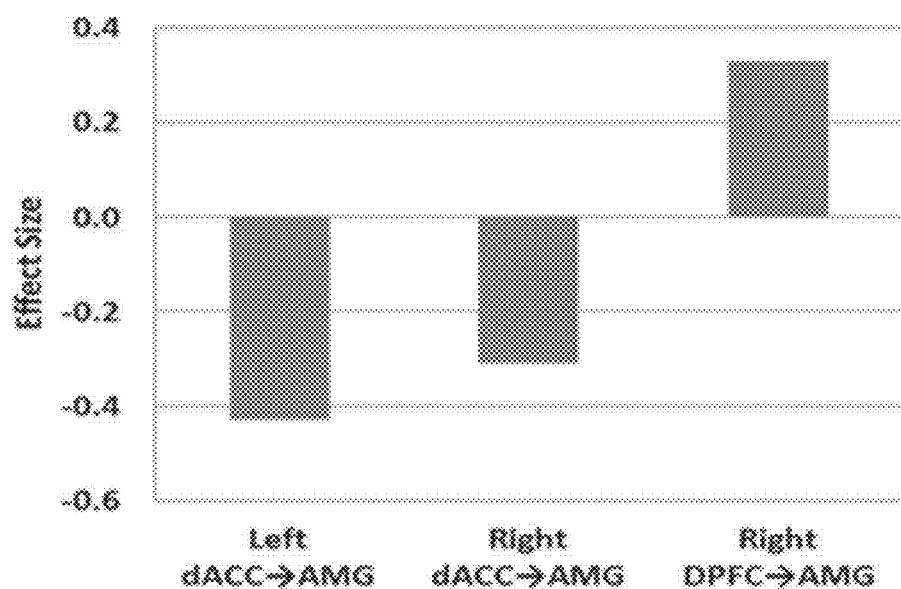

Effective Connectivity. Bilateral post-treatment reductions were observed in the effective connectivity from the dACC to the AMG (left: d=−0.44; right: d=−0.32) and right-sided increase in the top-down connectivity from the DPFC to the AMG (d=0.33) (FIG. 3). The post-treatment change in effective connectivity from both DPFC and DACC to the AMG correlated with a reduction in depressive symptoms as measured with the total score of the HAM-D, with the latter significant at an uncorrected threshold (r=0.51, p=0.05).

Figure 6:
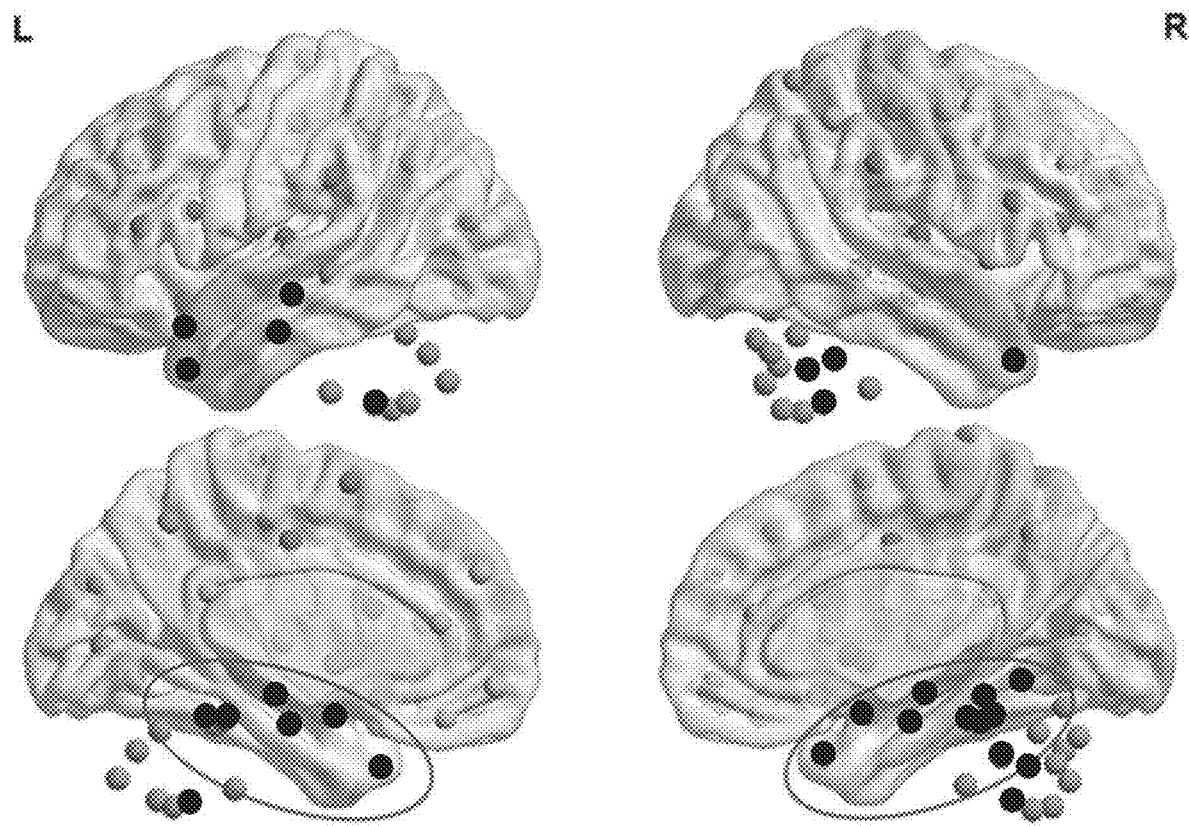
FIG. 6 shows a "community analysis" of healthy control subjects, wherein 1 color corresponds to 1 network. Healthy control subjects exhibit a normative medial temporal network (indicated by 7 black dots in left brain region surrounded by the solid oval and 12 black dots in right brain region surrounded by the solid oval) including the amygdala, hippocampi, parahippocampal gyri, temporal poles and some cerebellar vermis. fMRI images of subjects can be pre-processed and partitioned into voxels or regions. Activation within the regions can be quantified using time series data from fMRI images and a functional connectivity matrix can be calculated on which regional graph theory metrics can be applied to generate community of voxels or regions that appear connected.
Figure 7A:
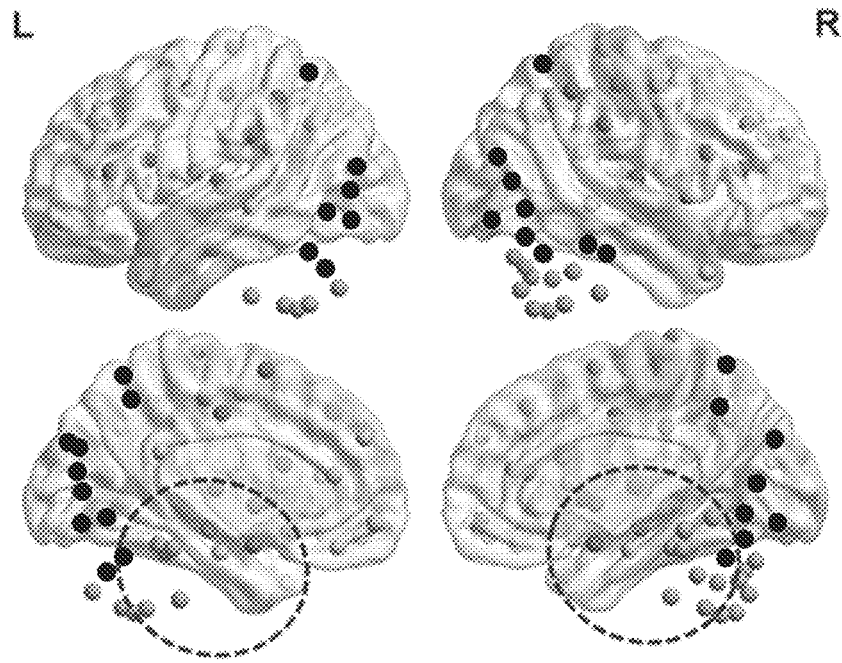
FIGS. 7A and 7B show a community analysis of seven MDD participants in the EFMT study. Prior to treatment, participants exhibit no medial temporal network (loss of black dots in left and right brain regions surrounded by the dashed circles). Following treatment, participants exhibited a partial medial temporal network (recovery of 8/18 total black dots in left and right brain regions surrounded by the dashed circles).
Figure 7B:
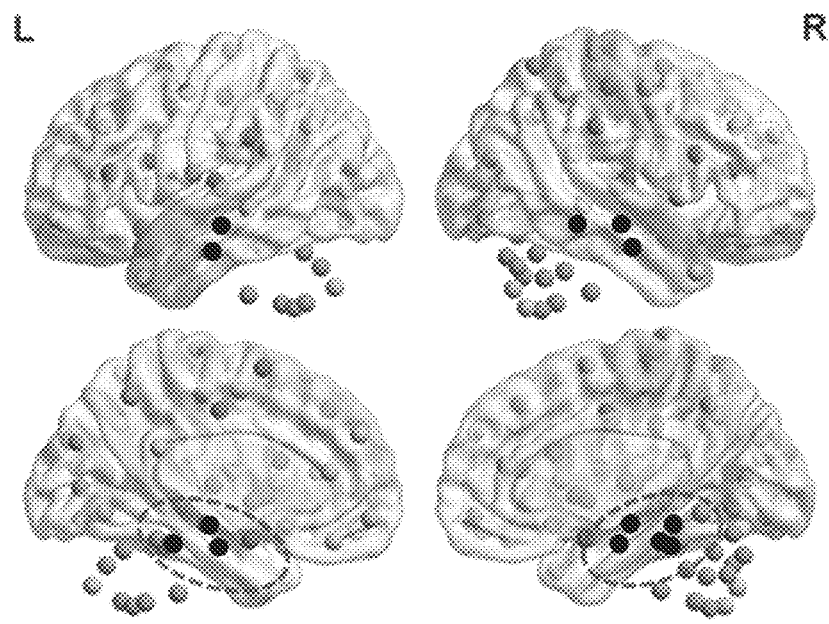

FIG. 6 provides a community analysis of 42 healthy control subjects, at rest. These data demonstrate that in healthy subjects the medial-temporal network (hippocampus-amygdala-temporal poles) are sufficiently integrated. FIGS. 7A-7B demonstrate a community analysis of 7 MDD participants from the EFMT study, at rest prior to treatment (left panel) and after treatment (right panel). These results demonstrate that MDD participants had a less-integrated medial-temporal network prior to EFMT treatment as evidenced by the absence of the black colored dot in left and right brain regions surrounded by the dashed circles, whereas EMFT-treatment partially restored the medial-temporal network of the MDD participants.

FIG. 6 provides a community analysis of 42 healthy control subjects, at rest. These data demonstrate that in healthy subjects the medial-temporal network (hippocampus-amygdala-temporal poles) are sufficiently integrated. FIG. 7 demonstrates a community analysis of 7 MDD participants from the EFMT study, at rest prior to treatment (left panel) and after treatment (right panel). These results demonstrate that MDD participants had a less-integrated medial-temporal network prior to EFMT treatment, whereas EMFT-treatment partially restored the medial-temporal network of the MDD participants.

The results presented herein demonstrate that EFMT training induces neuroplastic changes in patients with MDD. Previous studies have suggested a degree of lateralization in prefrontal dysfunction in MDD, with abnormalities in right DPFC being primarily associated with reduced voluntary control of emotional processing (Grimm et al. *Biol Psychiatry.* 63(4):369-76 (2008)). The results described herein demonstrate that the working-memory-induced modulation of the connectivity from the right DPFC to the right AMG was increased post-EMFT, which was associated with symptomatic improvement.

A further post-treatment change concerned the weakening of the functional coupling/effective connectivity between the dACC and AMG. Previous studies have suggested that the dACC shows maladaptive inflexibility in from the very early stages of MDD (Ho et al. *Neuropsychopharmacology.* 42(12):2434-2445 (2017)) because its connectivity does not show the expected variation across different tasks (Shine et al. *Neuron* 92: 544-554 (2016)). A weakening of the connectivity from the dACC to the AMG was observed post EFMT training, which was associated with symptomatic improvement. These data suggest that the reduction in the effective connectivity of the dACC following EFMT training may reflect a shift toward improved dACC functioning in MDD patients. The symptom improvement observed in this study appears to be associated with restoration of the regulatory control of limbic regions as indicated by increased DPFC and decreased dACC connectivity with AMG. See FIGS. 3A-3B.

Post-treatment reduction in the functional connectivity of the dDMN and SAL, and increased integration between networks involved in cognitive control and self-referential and salience processing was also observed. Hypoconnectivity and reduced integration of frontoparietal resting-state networks has been identified as a reliable correlate of MDD (Kaiser et al. *JAMA Psychiatry* 72: 603-611 (2015)). It is therefore interesting to note that most of the post-EMFT changes in between-network resting-state functional connectivity concern the CEN, which is considered a key network for cognitive control (Smith et al. *Proc Natl Acad Sci USA.* 106(31):13040-5 (2009)). The CEN was more integrated across the left and right hemisphere and with the DMN and SAL. This increase in the integration between networks for cognitive control, self-referential and salience processing has the potential to facilitate a more coherent and coordinated response to emotional stimuli in patients with MDD. Moreover, there was also evidence for post-treatment reduction in the functional connectivity of the dDMN, a phenomenon which has also been observed following successful treatment with antidepressants (Brakowski et al. *J Psychiatr Res.* 92:147-159 (2017)).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A system, comprising:
a data processing system comprising one or more processors, configured to:
maintain, on a hardware storage device, one or more data structures and executable logic defining classification rules, each data structure storing a plurality of keyed datasets, each of the plurality of keyed datasets including a respective key that represents a corresponding subject;
retrieve, from the at least one of the one or more data structures on the hardware storage device, a keyed dataset for a subject suffering from an affective disorder, the keyed dataset including a subject connectivity value derived from at least one of a scan or test provided to the subject represented by a key included in the retrieved keyed dataset, the subject connectivity value representing a magnitude of a connection associated with at least one sub-processing region of a nervous system of the subject in response to performing a cognitive-emotional training session at a first time, the at least one sub-processing region associated with a symptom of the affective disorder;
execute the executable logic against the keyed dataset to apply the classification rules to compare the subject connectivity value of the subject to a connectivity threshold value for the at least one sub-processing region to classify the subject as one of (i) a first classification to indicate that the subject is eligible for the cognitive-emotional training session at a second time and (ii) a second classification to indicate that the subject is ineligible for the cognitive-emotional training session at the second time;

determine that the subject connectivity value of the subject exceeds the connectivity threshold value for the at least one sub-processing region;

store, using the one or more data structures, an association between the key represented in the keyed dataset and a first classification value corresponding to the first classification to indicate that the subject suffering from the affective disorder is eligible for the cognitive-emotional training session at the second time, responsive to determining that the subject connectivity value exceeds the connectivity threshold value; and provide, responsive to the association between the key and the first classification value corresponding to the first classification indicating that the subject is eligible, an instruction for presentation of the cognitive-emotional training session to the subject at the second time, to induce activation of the at least one sub-processing region of the nervous system of the subject to address the symptom of the affective disorder.

2. The system of claim 1, wherein the at least one sub-processing region includes the dorsolateral prefrontal cortex (DPFC) and the amygdala (AMG), wherein the subject connectivity value and the connectivity threshold value represent an effective connectivity between the DPFC and the AMG and an effective connectivity threshold value between the DPFC and the AMG.

3. The system of claim 1, wherein the at least one sub-processing region includes the anterior cingulate cortex (dACC) and the amygdala (AMG), wherein the subject connectivity value and the connectivity threshold value, respectively, represent an effective connectivity between the dACC and the AMG and an effective connectivity threshold value between the dACC and the AMG.

4. The system of claim 1, wherein the at least one sub-processing region includes the default mode resting state network (DMN), wherein the subject connectivity value and the connectivity threshold value, respectively, represent a functional connectivity within the DMN and a functional connectivity threshold value associated with the DMN.

5. The system of claim 1, wherein the at least one sub-processing region includes the salience resting state network (SAL), wherein the subject connectivity value and the connectivity threshold value, respectively, represent a functional connectivity within the SAL and a functional connectivity threshold value associated with the SAL.

6. The system of claim 1, wherein the at least one sub-processing region includes the left central executive network (LCEN) and the right central executive network (RCEN), wherein the subject connectivity value and the connectivity threshold value, respectively, represent an integration between the LCEN and the RCEN and an integration threshold value between the LCEN and the RCEN.

7. The system of claim 1, wherein the at least one sub-processing region includes the dorsal default mode resting state network (dDMN) and the ventral default mode resting state network (vDMN), wherein the subject connectivity value and the connectivity threshold value, respectively, represent an integration between the dDMN and the vDMN and an integration threshold value between the dDMN and the vDMN.

8. The system of claim 1, wherein the at least one sub-processing region includes the left central executive network (LCEN) and the ventral default mode resting state network (vDMN), wherein the subject connectivity value and the connectivity threshold value, respectively, represent an integration between the LCEN and the vDMN and an integration threshold value between the LCEN and the vDMN.

9. The system of claim 1, wherein the at least one sub-processing region includes the left central executive network (LCEN) and the salience resting state network (SAL), wherein the subject connectivity value and the connectivity threshold value, respectively, represent an integration between the LCEN and the SAL and an integration threshold value between the LCEN and the SAL.

10. A method, comprising:

accessing, by a data processing system including one or more processors, a data structure including a subject identifier identifying a subject suffering from an affective disorder and a subject connectivity value derived from at least one of a scan or test provided to the subject, the subject connectivity value representing a magnitude of a connection associated with at least one sub-processing region of a nervous system of the subject in response to performing a cognitive-emotional training session at a first time, the at least one sub-processing region associated with a symptom of the affective disorder;

comparing, by the data processing system, that the subject connectivity value of the subject to a connectivity threshold value for the at least one sub-processing region to classify the subject as one of (i) a first classification to indicate that the subject is eligible for the cognitive-emotional training session at a second time and (ii) a second classification to indicate that the subject is ineligible for the cognitive-emotional training session at the second time;

determining that the subject connectivity value of the subject exceeds the connectivity threshold value for the at least one sub-processing region;

responsive to determining that the subject connectivity value exceeds the connectivity threshold value, storing, by the data processing system, in the data structure, an association between the subject identifier and a first classification value corresponding to the first classification to indicate that the subject suffering from the affective disorder is eligible for the cognitive-emotional training session at the second time; and providing, responsive to the association between the key and the first classification value corresponding to the first classification indicating that the subject is eligible, an instruction for presentation of the cognitive-emotional training session to the subject at the second time, to induce activation of the at least one sub-processing region of the nervous system of the subject to address the symptom of the affective disorder.

11. The method of claim 10, wherein the at least one sub-processing region includes the dorsolateral prefrontal cortex (DPFC) and the amygdala (AMG), wherein the subject connectivity value and the connectivity threshold value represent an effective connectivity between the DPFC and the AMG and an effective connectivity threshold value between the DPFC and the AMG.

12. The method of claim 10, wherein the at least one sub-processing region includes the anterior cingulate cortex (dACC) and the amygdala (AMG), wherein the subject connectivity value and the connectivity threshold value, respectively, represent an effective connectivity between the dACC and the AMG and an effective connectivity threshold value between the dACC and the AMG.

13. The method of claim 10, wherein the at least one sub-processing region includes the default mode resting state network (DMN), wherein the subject connectivity value and the connectivity threshold value, respectively, represent a functional connectivity within the DMN and a functional connectivity threshold value associated with the DMN.

14. The method of claim 10, wherein the at least one sub-processing region includes the salience resting state network (SAL), wherein the subject connectivity value and the connectivity threshold value, respectively, represent a functional connectivity within the SAL and a functional connectivity threshold value associated with the SAL.

15. The method of claim 10, wherein the at least one sub-processing region includes the left central executive network (LCEN) and the right central executive network (RCEN), wherein the subject connectivity value and the connectivity threshold value, respectively, represent an integration between the LCEN and the RCEN and an integration threshold value between the LCEN and the RCEN.

16. The method of claim 10, wherein the at least one sub-processing region includes the dorsal default mode resting state network (dDMN) and the ventral default mode resting state network (vDMN), wherein the subject connectivity value and the connectivity threshold value, respectively, represent an integration between the dDMN and the vDMN and an integration threshold value between the dDMN and the vDMN.

17. The method of claim 10, wherein the at least one sub-processing region includes the left central executive network (LCEN) and the ventral default mode resting state network (vDMN), wherein the subject connectivity value and the connectivity threshold value, respectively, represent an integration between the LCEN and the vDMN and an integration threshold value between the LCEN and the vDMN.

18. The method of claim 10, wherein the at least one sub-processing region includes the left central executive network (LCEN) and the salience resting state network (SAL), wherein the subject connectivity value and the connectivity threshold value, respectively, represent an integration between the LCEN and the SAL and an integration threshold value between the LCEN and the SAL.

19. The method of claim 10, wherein the subject connectivity value is a first subject connectivity value and the connectivity threshold value is a first connectivity threshold value, the method comprising:
accessing, by the data processing system, the data structure including a second subject connectivity value derived from at least one scan or test provided to the subject, the second subject connectivity value representing a magnitude of a connection associated with another at least one sub-processing region of the nervous system of the subject;
comparing, by the data processing system, the second connectivity value with the first connectivity threshold and a second connectivity threshold value for the other at least one sub-processing region;
responsive to determining that the first subject connectivity value exceeds the first connectivity threshold value and the second subject connectivity value is less than the second connectivity threshold value, storing, by the data processing system, in the data structure, the association between the subject identifier and the first classification value corresponding to the first classification to indicate that the subject suffering from the affective disorder is eligible for the cognitive-emotional training session; and
responsive to determining that the first subject connectivity value is less than the first connectivity threshold value and the second subject connectivity value exceeds the second connectivity threshold value, storing, by the data processing system, in the data structure, the association between the subject identifier and the second classification value corresponding to the second classification to indicate that the subject suffering from the affective disorder is ineligible for the cognitive-emotional training session.

20. The method of claim 19, wherein the at least one sub-processing region includes the dorsolateral prefrontal cortex (DPFC) and the amygdala (AMG), wherein the first subject connectivity value and the first connectivity threshold value represent an effective connectivity between the DPFC and the AMG and an effective connectivity threshold value between the DPFC and the AMG, wherein the another at least one sub-processing region includes the anterior cingulate cortex (dACC) and the amygdala (AMG), wherein the second subject connectivity value and the second connectivity threshold value, respectively, represent an effective connectivity between the dACC and the AMG and an effective connectivity threshold value between the dACC and the AMG.

* * * * *